(12) United States Patent
Suzuki et al.

US008993321B2

(10) Patent No.: US 8,993,321 B2
(45) Date of Patent: Mar. 31, 2015

(54) CONTAINER FOR PREPARING SERUM AND REGENERATIVE MEDICAL PROCESS USING THE SAME

(71) Applicant: JMS Co., Ltd., Hiroshima (JP)

(72) Inventors: Koji Suzuki, Hiroshima (JP); Junya Fujii, Hiroshima (JP); Mari Takabatake, Hiroshima (JP); Seishin Tanaka, Hiroshima (JP); Ken Kondo, Hiroshima (JP)

(73) Assignee: JMS Co., Ltd., Hiroshima (JP)

( * ) Notice: Subject to any disclaimer, the term of this patent is extended or adjusted under 35 U.S.C. 154(b) by 0 days.

(21) Appl. No.: 14/308,551

(22) Filed: Jun. 18, 2014

(65) Prior Publication Data

US 2014/0305876 A1     Oct. 16, 2014

Related U.S. Application Data

(62) Division of application No. 10/557,561, filed as application No. PCT/JP2004/007310 on May 21, 2004, now Pat. No. 8,796,017.

(30) Foreign Application Priority Data

May 21, 2003    (JP) .................................. 2003-144036

(51) Int. Cl.
| | | |
|---|---|---|
| *C12N 5/00* | (2006.01) | |
| *C12N 5/02* | (2006.01) | |
| *A61M 31/00* | (2006.01) | |
| *A61K 38/54* | (2006.01) | |
| *A61M 1/02* | (2006.01) | |

(52) U.S. Cl.
CPC ............. *A61M 1/0209* (2013.01); *A61M 1/029* (2013.01); *A61M 2202/0014* (2013.01); *A61M 2202/0415* (2013.01)
USPC ........ 435/372; 435/325; 424/93.72; 604/500; 604/507

(58) Field of Classification Search
None
See application file for complete search history.

(56) References Cited

U.S. PATENT DOCUMENTS

| | | | |
|---|---|---|---|
| 4,004,586 A | 1/1977 | Christensen et al. | |
| 4,189,382 A | 2/1980 | Zine, Jr. | |
| 4,807,676 A | 2/1989 | Cerny et al. | |
| 4,828,716 A | 5/1989 | McEwen et al. | |
| 4,892,537 A | 1/1990 | Carmen et al. | |
| 4,933,092 A | 6/1990 | Aunet et al. | |
| 4,983,779 A | 1/1991 | Schaap | |
| 5,431,201 A | 7/1995 | Torchia et al. | |
| 5,523,004 A | 6/1996 | Tanokura et al. | |
| 5,725,768 A | 3/1998 | Adachi et al. | |
| 6,258,778 B1 | 7/2001 | Rodgers et al. | |
| 6,325,750 B1 | 12/2001 | Jorgensen et al. | |
| 6,416,717 B1 | 7/2002 | Suzuki et al. | |
| 6,488,860 B2 | 12/2002 | Mari et al. | |
| 2002/0009394 A1 | 1/2002 | Koster et al. | |
| 2003/0008040 A1 | 1/2003 | Soeda et al. | |
| 2003/0012805 A1 | 1/2003 | Chen et al. | |
| 2003/0045857 A1 | 3/2003 | Dubrowny et al. | |
| 2003/0069601 A1 | 4/2003 | Nowakowski et al. | |
| 2003/0138910 A1 | 7/2003 | Reinecke et al. | |

FOREIGN PATENT DOCUMENTS

| | | |
|---|---|---|
| CN | 2482070 | 3/2002 |
| CN | 1389565 | 1/2003 |
| EP | 0 686 403 A1 | 12/1995 |
| GB | 2174149 | 10/1986 |
| JP | S53-12554 | 4/1978 |
| JP | S5616440 | 2/1981 |
| JP | S62148647 | 7/1987 |
| JP | S62-502594 | 10/1987 |
| JP | S62-502894 | 11/1987 |
| JP | H03504815 | 10/1991 |
| JP | H 04-024021 | 1/1992 |
| JP | H04-083165 | 3/1992 |
| JP | H06-51048 | 7/1994 |
| JP | H06-197887 | 7/1994 |
| JP | H07-185393 | 7/1995 |
| JP | 2553404 | 11/1996 |
| JP | H09-108333 | 4/1997 |

(Continued)

OTHER PUBLICATIONS

Matsuura and Tanaka, Affidavit Under Rule 1.132 in U.S. Appl. No. 10/557,561, Jul. 28, 2010, 6 pgs.*
PCT International Search Report issued to PCT Application No. PCT/ JP2004/007310, mailed Sep. 7, 2004, 8 pages.
Office Action issued to U.S. Appl. No. 10/557,561, mailed Mar. 20, 2007, 6 pages.
Office Action issued to U.S. Appl. No. 10/557,561, mailed Jan. 9, 2008, 5 pages.
Notice of Reasons for Rejection issued to CN Application No. 200480013939.6, mailed Aug. 29, 2008, 10 pages.
Office Action issued to U.S. Appl. No. 10/557,561, mailed Mar. 9, 2009, 16 pages.

(Continued)

*Primary Examiner* — Thane Underdahl
(74) *Attorney, Agent, or Firm* — Muncy, Geissler, Olds & Lowe, P.C.

(57) ABSTRACT

A blood storage container suitable for quick and efficient production of a large amount of serum while ensuring high safety, and a method of separating blood and a regenerative medical process using the same are provided. A blood component separation storage apparatus is provided for separating a plurality of blood components of blood so as to be stored therein. The blood component separation storage apparatus includes a blood reservoir for holding the blood and a component storage part connected to the blood reservoir aseptically and in an air-tight manner. The blood reservoir contains an anticoagulant which suppresses coagulation of the blood. The blood reservoir has a serum producing function to remove coagulation factors from the blood to an extent enabling use in practical applications as a serum, and the component storage part stores each blood component generated by separation of the blood in the blood reservoir.

6 Claims, 31 Drawing Sheets

(56) References Cited

FOREIGN PATENT DOCUMENTS

| | | |
|---|---|---|
| JP | H 09-206371 | 8/1997 |
| JP | H09-511152 | 11/1997 |
| JP | H 10-236976 | 9/1998 |
| JP | H 10-279489 | 10/1998 |
| JP | H 11-246421 | 9/1999 |
| JP | 2000000228 | 1/2000 |
| JP | 2000-504945 | 4/2000 |
| JP | 2000-511531 | 9/2000 |
| JP | 2001275662 | 10/2001 |
| JP | 2001299730 | 10/2001 |
| JP | 2002-538900 | 11/2002 |
| JP | 2002-540818 | 12/2002 |
| JP | 2003/10309 | 1/2003 |
| JP | 2004-269409 | 9/2004 |
| WO | WO 86/07054 | 12/1986 |
| WO | WO 90/07876 | 7/1990 |
| WO | WO 95/12973 | 5/1995 |
| WO | WO 97/07836 | 3/1997 |
| WO | WO 97/43899 | 11/1997 |
| WO | WO 00/46249 | 8/2000 |
| WO | WO 01/28621 | 4/2001 |
| WO | WO 02/081007 | 10/2002 |

OTHER PUBLICATIONS

Notice of Reasons for Rejection issued to CN Application No. 200480013939.6, mailed Feb. 20, 2009, 7 pages.
Office Action issued to U.S. Appl. No. 10/557,561, mailed Jul. 21, 2009, 12 pages.
ChemIndustry.com; "Diatomaceous silica" http://www.chemindustry.com/chemicals/993198.html accessed Jul. 13, 2009 2:44:00, 2 pages.
G.V.R. Born and M.J. Cross; "The Aggregation of Blood Platelets" J Physiol. (1963), 168, pp. 178-195.
Office Action issued to U.S. Appl. No. 10/557,561, mailed Feb. 2, 2010, 15 pages.
Nigel Mils "Case Study: Materials for Blood Bags" copyright 2002 Centre for Materials Education, 6 pages.
Notice of Reasons for Rejection issued to JP Application No. 2007-093087, mailed Apr. 20, 2010, 3 pages.
Notice of Reasons for Rejection issued to JP Application No. 2007-093088, mailed Apr. 20, 2010, 3 pages.
Notice of Reasons for Rejection issued to JP Application No. 2007-093089, mailed Apr. 20, 2010, 3 pages.
Notice of Reasons for Rejection issued to CN Application No. 200910009532.0, mailed Nov. 16, 2011, 14 pages.
Supplemental European Search Report issued to EP Application No. 04734398.3, mailed Mar. 9, 2012, 5 pages.
Notice of Reasons for Rejection issued to JP Application No. 2011-053446, mailed Oct. 16, 2012, 5 pages.
Notice of Reasons for Rejection issued to JP Application No. 2010-138703, mailed Oct. 16, 2012, 5 pages.
Office Action issued to U.S. Appl. No. 10/557,561, mailed Apr. 30, 2008, 11 pages.
Rapaport et al., "The Effect Of Glass Upon The Activity Of The Various Plasma Clotting Factors", J Clin Invest. Jan. 1995; 34(1): 9-19.
Hedenius "An Improved Blood Coagulation Time Apparatus", Scand J Clin Lab Invest. 1951; 3(1):80-1.
Office Action issued Feb. 2, 2015 in co-pending U.S. Appl. No. 14/308,607, 11 pgs.

* cited by examiner

CONTAINER FOR PREPARING SERUM AND REGENERATIVE MEDICAL PROCESS USING THE SAME

CROSS REFERENCE TO RELATED APPLICATIONS

This application is a Divisional of co-pending application Ser. No. 10/557,561, filed on Nov. 21, 2005, which is a 371 of PCT/JP04/07310, filed May 21, 2004, for which priority is claimed under 35 U.S.C. §120; and this application claims priority of Application No. 2003-144036 filed in Japan on May 21, 2003 under 35 U.S.C. §119, the entire contents of all of which are hereby incorporated by reference.

TECHNICAL FIELD

The present invention relates to blood storage containers, and relates to methods of separating blood and regenerative medical process using the same.

BACKGROUND ART

Currently, in the field of regenerative medicine, studies in which stem cells collected from a subject are caused to proliferate or differentiate ex vivo, and are thereafter transplanted into a subject, thereby promoting regeneration of tissue of the subject have been carried out. Stem cells are multipotent and can differentiate into a variety of tissues and organs, and they have been attracting attention as cells which are key to regenerative medicine.

It has been known that in ex vivo cultural proliferation of stem cells, addition of a serum to the medium is effective. However, when human therapies are targeted, use of a serum derived from an animal other than from the human body should be avoided in light of possible problems of safety. Therefore, use of a serum prepared from blood which is derived from a human, in particular, which was collected from the same subject has been desired. In addition, culture of stem cells in the field of regenerative medicine requires relatively larger amounts of serum in comparison with blood tests.

As a method of preparing such a serum, a method in which a blood collection tube is used that contains a blood coagulation accelerating substance, such as glass powder is disclosed in JP-A No. 2000-000228.

DISCLOSURE OF THE INVENTION

However, the method described in JP-A No. 2000-000228 uses a blood collection tube with a low capacity aimed at blood tests, and therefore, preparatory procedures must be repeated many times to prepare a serum in amounts required for culture of stem cells. Hence, this method is not suited for practical applications.

Additionally, prepared serums are often temporarily preserved by chilling or freezing until use. Hence, a procedure for transferring from the blood collection tube to a container for preservation is required. Repetition of such a procedure may increase the probability of contamination of the serum by microorganisms. Furthermore, a serum separating agent is often added to such blood collection tubes, therefore, possible contamination of the serum with an impurity derived from this serum separating agent cannot be reliably avoided. Accordingly, also in terms of safety and hygiene, use of the method disclosed in JP-A No. 2000-000228 is not suitable for the field of regenerative medical for humans. Moreover, according to existing blood collection tubes for preparing a serum, recovery of components other than the serum is difficult due to the structure of the blood collection tube, and in addition, recycling thereof is impossible because such components form clots.

As described above, development of a container for preparing a serum has been desired which is suitable for preparing large amounts of serum for culturing stem cells.

The present invention was achieved in view of the foregoing problems. Thus, an object of the present invention is to provide a blood storage container suitable for quick and efficient production of a large amount of serum while securing high safety, and a method of separating blood and a regenerative medical process using the same.

In order to accomplish the aforementioned object, the present invention provides a blood component separator having a serum producing function which produces serum in practical usable amounts in the presence of humoral components and platelets derived from the blood, by a coagulation activating action.

The term "blood" used herein means whole blood including hemocytes (erythrocytes, leucocytes, platelets) and plasma (serum) that is a liquid component, and liquid containing at least one of these (for example, blood collected by apheresis). Furthermore, the term "serum" means a pale yellow liquid obtained by allowing collected blood to stand, resulting in reduction of the fluidity, followed by separation from the red coagulated block (clot). The "serum" according to the present invention is different from common serums in terms of the production process without including separation from the clot, but it means a humoral component in the blood that is useful in cell culture and that includes coagulation factors and growth factors substantially equivalent to those in common serums.

The term "humoral component derived from blood" means "blood components other than hemocytes" or "mixture of blood components other than hemocytes and an agent such as an anticoagulant added thereto".

The term "coagulation activating action" means activation of coagulation factors in the blood to eliminate the coagulation factors from the blood.

The term "serum producing function which produces a serum in a practically usable amount" means, for example, an amount which can be used in culturing stem cells. In culturing stem cells, a serum is required in an amount of approximately 10% of the medium. Therefore, the amount is preferably from 5 ml and to 1000 ml, and more preferably from 10 ml to 600 ml.

Specifically, the following is provided.

The present invention provides a blood component separator, an apparatus for separating collected blood into a plurality of blood components and storing them, the apparatus comprising a blood reservoir for holding the blood, having serum producing function to eliminate coagulation factors from the blood in order to prepare a serum in a practical usable amount.

According to the blood component separator described above, collected blood can be held in large amounts in the blood reservoir by having the blood reservoir. Additionally, because a serum producing function is provided to this blood reservoir, rapid activation of platelets and coagulation factors in the blood is made possible. Furthermore, because these factors to be activated can be rapidly eliminated, large amounts of serum can be prepared. This blood component separator preferably comprises a component storage part for storing a plurality of blood components separated from the blood. It is more preferred that this component storage part and the blood reservoir be aseptically connected in an airtight manner. Accordingly, a series of steps, from collection of the blood to preparation of the serum, can be carried out without exposure to the air outside. Therefore, the risk of contamination by microorganisms can be reduced.

The blood component separator according to the present invention can also be used as a blood component separator for use in nonhuman, because it can be used not only for human blood but also for the blood of mammals such as rodents, livestock, and primates.

In the aforementioned blood component separator, the plurality of blood components may include a serum, and may include leukocytes and erythrocytes.

According to the present invention, the serum separated by the blood component separator contains many cell growth factors, and therefore, it is suited for use in the field of regenerative medicine. In addition, because factors to be activated can be separately recovered, effective utilization of the collected blood is permitted without discarding the same.

In the aforementioned blood component separator, the blood reservoir and the component storage part are flexible bags, and the aforementioned serum producing function may be provided by a blood coagulation accelerating substance disposed inside the blood reservoir.

The blood reservoir and the component storage part are flexible bags which are lightweight and portable. At least one of each is provided, but pluralities thereof also may be provided. It is preferred that one blood reservoir and two or more component storage parts be provided. Furthermore, each volume is not particularly limited as long as they can substantially separate each blood component from the blood, but is preferably from 5 (ml) to 1000 (ml), and particularly preferably from 10 (ml) to 600 (ml). In addition, by providing a blood coagulation accelerating substance inside this blood reservoir, the serum producing function can be imparted. The blood coagulation accelerating substance is included to an extent to enable removal of the blood coagulation factors such as fibrin and platelets from the blood. Furthermore, because the blood coagulation accelerating substance is insoluble in blood, the contamination of impurities in the resulting serum can be avoided.

In the blood component separator, it is preferred that the blood coagulation accelerating substance be insoluble in the aforementioned blood, and have a block-like shape. Also, it is more preferred that the blood coagulation accelerating substance be provided in a freely movable manner in the blood reserved in blood reservoir.

According to this invention, handling during manufacture can be improved by employing the blood coagulation accelerating substance having the shape of particles or granules, or blocks. Additionally, by providing the blood coagulation accelerating substance to be freely movable, much smoother contact with the blood is enabled, and the efficiency of the blood activation can be improved.

In the aforementioned blood component separator, the specific gravity of the blood coagulation accelerating substance may be greater than the aforementioned each blood component separated from the blood. Hence, the prepared serum can be readily removed from the blood reservoir.

Moreover, when a serum is prepared from the blood, centrifugal separation should be carried out after the activation of the factors to be activated such as platelets and blood coagulation factors. However, in order to reduce damage to erythrocytes (hemolysis) and breakage of the blood reservoir in this case, appearing shape of the blood coagulation accelerating substance is preferably formed to be nearly spherical. Furthermore, with the aim of rapid activation, the surface of the blood coagulation accelerator is preferably formed with a layer comprising a silicon dioxide compound.

Examples of the silicon dioxide compound which may be used include at least one or more selected from glass, silica, diatomaceous earth, kaolin and the like, but this is not limited thereto.

Moreover, when a magnet is used as a core of the blood coagulation accelerator, stirring of the blood can be effected by allowing a magnetic field to act on the blood reservoir, thereby permitting the factors to be activated to be rapidly activated.

The blood coagulation accelerating substance preferably has a porous structure in order to execute activation, because great surface area per unit volume can be provided. However, in this instance, it is necessary to ensure penetration of blood into the pores.

In connection with the blood coagulation accelerating substance in the blood reservoir, to define the surface area to satisfy the relationship of from $0.1$ $mm^2/ml$ to $25$ $mm^2/ml$ in the volume of the blood which can be reserved in the blood reservoir is preferred in light of both terms of promotion of activation and suppression of hemolysis. This definition corresponds to the best condition value at present; however, values outside this range are within the scope of the present invention as long as similar effects are achieved.

In the aforementioned blood component separator, the blood reservoir may or may not be charged with a serum separating agent.

Also, in the blood component separator, at least two connection ports are formed at the blood reservoir. Among the two connection ports, one may be connected in an air-tight manner to an introducing path for introducing the blood to the blood reservoir, while another may be connected in an air-tight manner to a discharging path for discharging each blood component separated from the blood in the blood reservoir.

According to this invention, connection of the introducing path and discharging path to the connection ports formed at the blood reservoir can protect the serum from contamination with blood components.

In the aforementioned blood component separator, the component storage part comprises two or more bags. The discharging path is constituted with a plurality of discharge tubes connected to each bag. At least a part of the plurality of discharge tubes may be used in combination.

According to this invention, due to the component storage part comprising two or more bags, and at least a part of the plurality of discharge tubes being used in combination, respective bags are connected together, thereby facilitating handling. In addition, by air tight connection of each part in this manner, contamination by microorganisms can be prevented.

In the aforementioned blood component separator, the blood reservoir may contain air. The air contained in the blood reservoir is preferably from $0.03$ cc/ml to $1$ cc/ml per the volume of the reservable blood.

According to this invention, inclusion of the air in the blood reservoir enables achieving an effect that is similar to the case in which the blood coagulation accelerating substance is included.

Furthermore, the method of separating blood of the present invention is characterized in that the blood is separated into humoral components and nonhumoral components in the presence of the humoral components and the platelets derived from the blood using the blood component separator to which a serum producing function which produces a serum in a practically usable amount is imparted by a coagulation activating action.

Specifically, the following method is provided.

A method of separating blood in which an apparatus for separating collected blood into a plurality of blood components and storing them is used, the apparatus being a blood component separator comprising a blood reservoir for holding the blood to which a serum producing function that produces a serum in a practically usable amount as a serum is imparted, and the method comprising a reservation step of reserving the collected blood in the blood reservoir, an activation promoting step of initiating the serum producing function and promoting activation of factors to be activated including platelets and coagulation factors in the blood reserved in the blood reservoir, and a separation step of separating the factors to be activated from the blood which were activated and agglutinated in the activation promoting step.

In the above method of separating blood, the activation promoting step may be a step of shaking the blood component separator.

Furthermore, in the above method of separating blood, the serum producing function may be provided by a blood coagulation accelerating substance provided inside of the blood reservoir.

Moreover, in the above method of separating blood, each blood component discharged in the discharge step may include a serum.

Additionally, in the method of separating blood, the discharging step may be a step of storing the blood components in the component storage part by letting the liquid components in each blood flow in the state of the blood coagulation accelerating substance fixed.

Furthermore, in the above method of separating blood, the blood coagulation accelerating substance in the discharging step may be fixed by a fixing device mounted on at least one of the interior or the exterior of the blood reservoir.

Furthermore, in the method of separating blood, the fixing device may be one or more selected from the group consisting of magnets, clamps, holding parts that hold the blood reservoir, and a plurality of protrusions disposed in the blood reservoir.

According to such an invention, collection of a large amount of blood at a time and quick separation are made possible. Moreover, because the process from the reservation step to the introduction step can be conducted without exposing to the outside air, risk of contamination by microorganisms can be reduced. Furthermore, the method may comprise a discharging step of discharging each blood component, other than the factor to be activated separated from the blood in the separation step, to the component storage part.

In the activation promoting step, the factor to be activated can be activated by shaking the entirety of the blood component separator or the blood reservoir. Although the method of the shaking is not particularly limited as long as hemolysis is not caused, it is preferably conducted at a speed of shaking which allows the blood coagulation accelerating substance to evenly move in the blood. Also, in the case in which a blood coagulation accelerating substance including a magnet used as a core is used, stirring of the blood can be performed by allowing a magnetic field to act on the blood reservoir.

In the separation step, fibrin is generated in the state of the activated factor to be activated being adhered to the blood coagulation accelerating substance. Accordingly, recovery of the serum is facilitated. Also, in the discharging step, recovery of erythrocytes is further facilitated by fixing a blood coagulation accelerating substance, to which fibrin was adhered, by a fixing device.

Furthermore, the present invention provides the following method of recovering fibers in blood and regenerative medical process.

A method comprises: separating blood into humoral components and nonhumoral components using a blood component separator to which a serum producing function which produces a serum in a practically usable amount in the presence of humoral components and platelets derived from blood is imparted by a coagulation activating action; and recovering fibers from the nonhumoral components.

A regenerative medical process comprises: separating blood into humoral components and nonhumoral components using a blood component separator to which a serum producing function which produces a serum in a practically usable amount in the presence of humoral components and platelets derived from the blood is imparted by a coagulation activating action; adding the humoral components to a medium; culturing by inoculating cells collected from a subject to this medium; and preparing thus resulting cell or tissue for transplantation to the subject.

In the aforementioned regenerative medical process, the humoral components may include a serum.

A regenerative medical process comprises: separating blood into humoral components and nonhumoral components using a blood component separator to which a serum producing function which produces a serum in a practically usable amount in the presence of humoral components and platelets derived from the blood is provided by a coagulation activating action; adjusting the concentration of the nonhumoral components; and thereafter preparing for blood transfusion to the subject.

In the method of separating blood, the nonhumoral components may contain a serum, leukocytes and erythrocytes.

Use of these methods enables preparation of a large amount of serum, and therefore, preparation of autoserum in an amount required for cell culture is permitted. Furthermore, also in the case in which blood transfusion is required in surgery, because erythrocytes and fibrin can be recovered after collecting the serum, autotransfusion after adjusting the concentration, use of the fibrin as a scaffold of stem cells or a barrier of wounds and the like can be performed.

As explained in the foregoings the blood component separator of the present invention is used for separating the collected blood into each component. Because it has a blood reservoir for holding the blood, and a serum producing function is provided to this blood reservoir, a serum in which propagation of microorganisms is suppressed can be prepared quickly and in large amounts. Thus, it is suited for preparation of large amounts of serum which may be used in stem cell culture in regenerative medicine. Additionally, erythrocytes and other components after collecting the serum are suited for use as the blood for autotransfusion and as a barrier for wounds.

Therefore, when the blood component separator according to the present invention is used, large amounts of blood components including serum can be prepared (produced) quickly and efficiently from the collected blood while ensuring high safety.

Also, in the method of separating blood of the present invention, the blood component separator according to the present invention described above is used, the method comprises: a holding step of holding the collected blood in the blood reservoir; an activation promoting step of initiating the serum producing function and promoting activation of factors to be activated including platelets and coagulation factors in the blood held in the blood reservoir; and a separation step of separating from the blood the factors to be activated which were activated and agglutinated in the activation promoting step, and further comprises, as needed, recovering the blood components remaining after the serum collection, and preparing for use in autologous blood transfusion and as a scaffold of stem cells or a barrier for wounds.

Therefore, when this method of preparing a serum is used, blood components which are highly safety can be produced in large quantities.

Also, the regenerative medical process of the present invention comprises: adding the serum prepared using the method of separating blood described above to a medium; culturing by inoculating stem cells collected from a subject to this medium; and preparing the cells or the tissue obtained by the culture for transplantation to the subject of therapy. In addition, when the subject is a patient with low volume of circulating blood, such as a child, or when heavy bleeding in transplantation is feared, the recovered erythrocytes may be subjected to transfusion, or fibrin may be used as a scaffold of the transplanted site or as a barrier of the transplanted site.

Accordingly, use of this regenerative medical process enables use of a large amount of serum with biological safety ensured. Hence, tissues and functions of the subject can be regenerated safely and certainly.

BEST MODE FOR CARRYING OUT THE INVENTION

Figure 1:
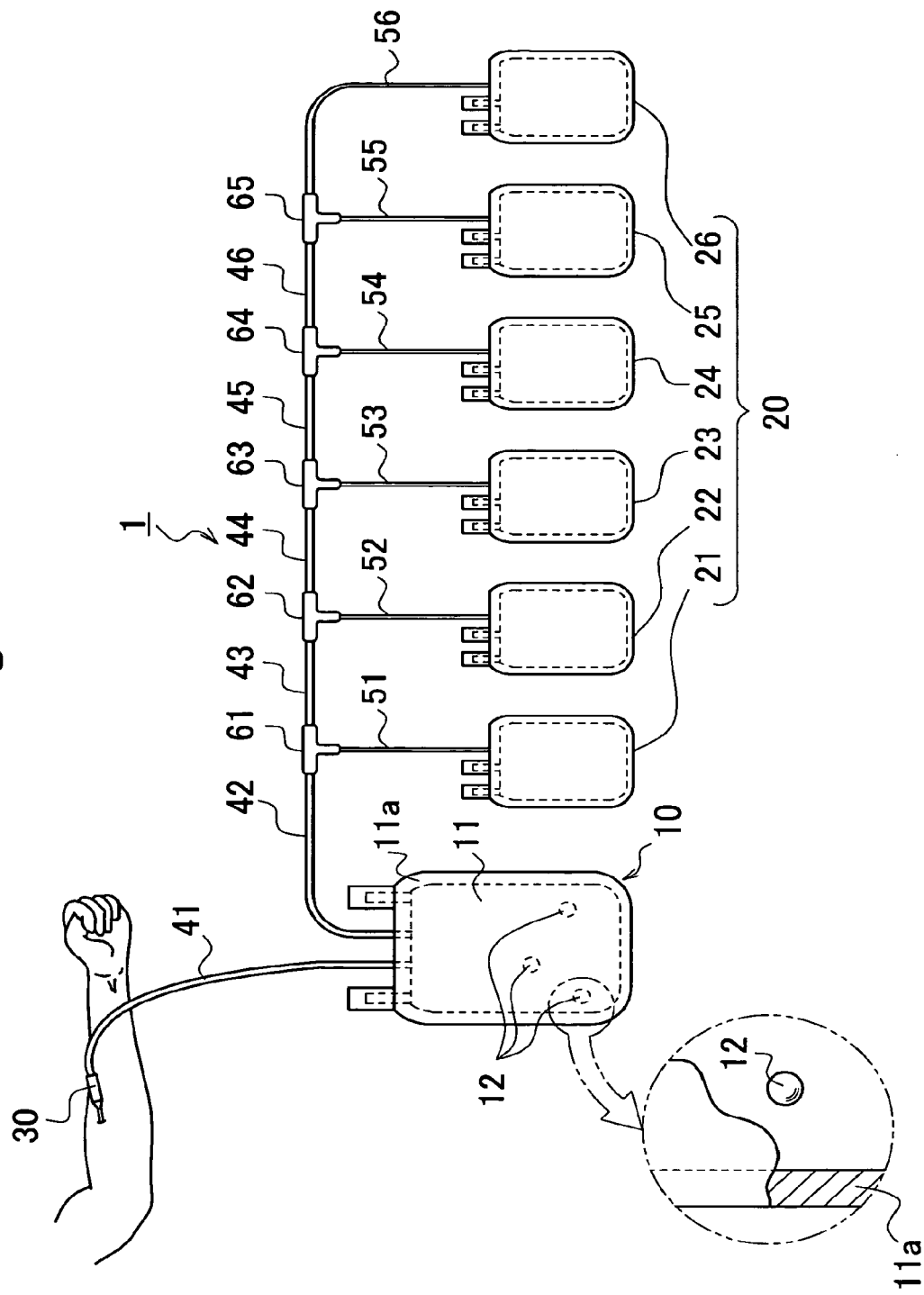
FIG. 1 is a view illustrating a blood component separator according to a first Embodiment of the present invention.

The blood component separator according to the present invention is an apparatus which can produce a serum in a practically usable amount by providing a blood coagulation accelerating function to a place for reserving blood components to produce the serum.

In a suggested typical example of the mode of the apparatus, at least one or more flexible bags are connected aseptically in a liquid-tight and air-tight manner, to which a blood coagulation accelerating function is provided.

Such a blood component distribution and storage apparatus has a form in appearance that is similar to blood bag or separation bag generally referred to. Such a form that is similar to these was adopted because of performances exhibited for many years to demonstrate that these are suited forms for distributing collected various types of components aseptically in a liquid-tight and air-tight manner.

Additionally, the aspect of imparting a blood coagulation accelerating function relates to an essential feature of the present invention. Even in the case of a mere flexible bag, a serum can be produced through activation of blood coagulation factors over time when humoral components including the coagulation factors are stored. However, in addition to the necessity of a relatively long time, growth factors included in the serum have come to be inactivated, and thus resulting activity is insufficient. Hence, the blood coagulation accelerating function is provided. Accordingly, humoral components including the blood coagulation factors and the blood coagulation factors are brought into contact in the above place, thereby accelerating blood coagulation rapidly. As a result, preparation of the serum can be carried out in an extremely short period of time, and the serum can be prepared in a state with suppression of decreased activity. This event is applicable also to the cases in which the bag itself is formed with a material having a blood coagulation accelerating function. Therefore, such modes are not excluded from the present invention. In other words, a principle of the present invention also involves modes having a reservoir space wall formed with a material having a high blood coagulation accelerating function in comparison with medical materials generally used for blood bags, separation bags, and the like.

Examples of the substance having a blood coagulation accelerating function which has been verified to have the highest effect at present include glass processed bodies. It is conventionally known that glasses have a blood coagulating action; however, there is not yet any example of positive use thereof for producing a relatively large amount of serum. The present inventors tried to use a glass processed body as a substance having a blood coagulation accelerating function to allow it to exist in blood components that produce a serum, and repeated mutual contact. Consequently, a large amount of serum was successfully produced in a short period of time without decreasing the activity.

Additionally, as a substance having a blood coagulation accelerating function, air was used in place of the aforementioned glass processed body. It is already known that blood is coagulated upon contact with the air; however, no example is known in which the air is positively used for producing a serum. Thus, attempts to bring the blood into contact with the air as a substance having a blood coagulation accelerating function were repeated, and also, a large amount of serum was successfully produced in a short period of time.

It has been revealed that the substance having a blood coagulation accelerating function is activated to a greater extent as the contact with the blood is increased. More specifically, it has been revealed that in the case of the glass processed body, to give greater specific surface area will be effective, while in case of the air, giving greater content will be effective. However, when a substance is used as a substance having a blood coagulation accelerating function such as a glass processed body, fears of hemolysis must be considered.

Next, the following mode is suggested as a mode to bring humoral components containing blood coagulation factors into contact with a substance having a blood coagulation accelerating function (hereinafter, referred to as "blood coagulation accelerating substance").

In the first mode, the blood collected from a human body is reserved in a blood reservoir holding a blood coagulation accelerating substance to promote coagulation of the blood, thereby separating a serum.

In this operation, the separated serum is transferred aseptically to a bag other than the blood reservoir to be preservable in this bag. Alternatively, the separated serum may be aseptically discharged outside to a subject for use as an addition to a cell culture system as a growth factor. Also, other blood components separated concomitantly with separation of the serum (erythrocytes, fibrin, and the like) can be used for blood transfusion or regeneration therapy.

Second, a mode is suggested in which the blood collected from a human body is reserved in a blood reservoir, and after separating blood components in the state of this reservoir including anticoagulant added thereto, platelets and humoral components including blood coagulation factors which are components that produce a serum, among the separated components, are aseptically transferred into separate bags, and a serum may be produced in this bag. In this instance, although the aforementioned blood coagulation accelerating substance should be stored in the bag for producing a serum, as a matter of course, function of the stored coagulation accelerating substance can be sufficiently fulfilled by adding a neutralizing agent for neutralizing the contaminated anticoagulant. In this procedure, the separated serum may be preserved in the blood reservoir without modification, or may be aseptically transferred to and preserved in another bag. The separated serum may be aseptically discharged outside to uses such as addition to a cell culture system as a growth factor. Also, other blood components separated before and after separation of the serum (erythrocytes, fibrin and the like) can be used for blood transfusion or regeneration therapy.

The third mode has a relationship with the second mode. In this mode, the serum is produced in a similar manner to the second mode after collecting only the components that produce the serum from the blood before the introduction to the aforementioned apparatus. In this mode, so called apheresis is carried out in the first place, and therefore, unnecessary components can be immediately returned to the subject in case in which collection of the serum or fibrin alone is intended. Accordingly, a physical burden imposed on the subject can be diminished.

Hereinafter, the present invention will be explained in more detail.

First Embodiment

Overall Constitution of Blood Component Separator 1

Constitution of a blood component separator 1 according to this Embodiment will be explained with reference to FIG. 1. In FIG. 1, only a principal part in the constitution of the blood component separator 1 is extracted and illustrated.

As shown in FIG. 1, the blood component separator 1 according to this Embodiment is constituted from a blood reservoir 10 and a component storage part 20 as main elements. Among these, the blood reservoir 10 is constituted from a main body part 11 formed with two sheets of a flexible resin material, for example, soft polyvinylchloride, by fusion at the external marginal part 11a to yield a bag shape, and a glass processed body 12 disposed inside of the main body part 11. In other words, the blood reservoir 10 has a constitution including glass processed bodies 12 as a blood coagulation accelerating substance stored inside of the main body part 11 as an exterior package.

The blood reservoir 10 is similar to so-called blood bag and transfer bag in respect of inner volume and shape in the main body part 11; however, it is different from the blood bag in terms of absence of an anticoagulant filled therein, and also different from transfer bag in terms of inclusion of a coagulation accelerating agent. In addition, the inside of the blood reservoir 10 is previously subjected to a sterilization.

The glass processed bodies 12 in the main body part 11 have a substantially spherical shape and consists of, for example, soda glass. Also, FIG. 1 shows a constitution having three glass processed bodies 12 in the blood reservoir 10; however, it is preferred to define the surface area of the glass processed body 12 to satisfy a relationship to the volume of reservable blood to be 0.1 $mm^2$/ml or greater, in terms of achieving a blood coagulation accelerating function.

The glass processed bodies 12 are not joined to the inner wall of the main body part 11 or the like, but are provided to give a freely movable state in the main body part 11 when a shaking action, a vibrating action, or the like is applied to the main body part 11.

Moreover, in order to suppress breakdown of erythrocytes in the blood which may lead to hemolysis when a shaking action, a vibrating action or the like is applied to the main body part 11 after holding the blood, and furthermore, when the blood is subjected to a centrifugal separator, it is preferred to provide the glass processed body 12 with the surface area to satisfy a relationship of the surface area thereof to the volume of reservable blood in the main body part 11 of the blood reservoir 10 to be 25.0 $mm^2$/ml or less. Grounds of the preference of these ranges will be described later.

The component storage part 20 is constituted from 6 bags 21 to 26, each being made with soft polyvinylchloride. These are previously subjected to a sterilization.

As shown in FIG. 1, two tubes 41 and 42 are connected in an air-tight manner at the upper edge end of the main body part 11 of the blood reservoir 10 to the connection ports thereof, respectively. The tube 41 among them plays a role as an introducing path for introducing the blood, and therefore, a needle for collecting blood 30 or a junction which can be connected to a needle for collecting blood is connected at the other end. Another tube 42 connected in an air-tight manner to the blood reservoir 10 is connected to each of the bags 21 to 26 via tubes 43 to 46 and 51 to 56, and branches 61 to 65. These play a role as discharging path for discharging separated blood components. These tubes 41 to 46 and 51 to 56 are constituted from a resin material having flexibility, for example, a material such as soft polyvinylchloride or the like.

In this constitution, the bags 21 to 26 and each tube 51 to 56 of the component storage part 20 are also connected in an air-tight manner.

Additionally, regarding the dimensions of the tubes 41 and 42, the inner diameter size is defined to be smaller than the external diameter size of the glass processed body 12. This prevents the glass processed body 12 from gaining entry into the tubes 41 and 42 when the serum is prepared and discharged.

The blood reservoir 10, and the bags 21 to 26 and each of the tubes 41 and 42, and 51 to 56, are connected in a state to make the inner space inaccessible to the external environment. Also, each of the tubes 42 to 46 and 51 to 56 and each of the branches 61 to 65 are connected in states to make the inner region where the serum circulates inaccessible to the external environment. Specifically, they are connected by solvent adhesion, thermal welding, ultrasound welding or the like.

Although not shown in FIG. 1, the blood component separator 1 according to this Embodiment is constituted to be able to switch the flow channel when the blood and the extracted serum are discharged through pinching the necessary site of each tube 42 to 46, and 51 to 56, with a clamp.

Operation for Serum Preparation

Figure 2:
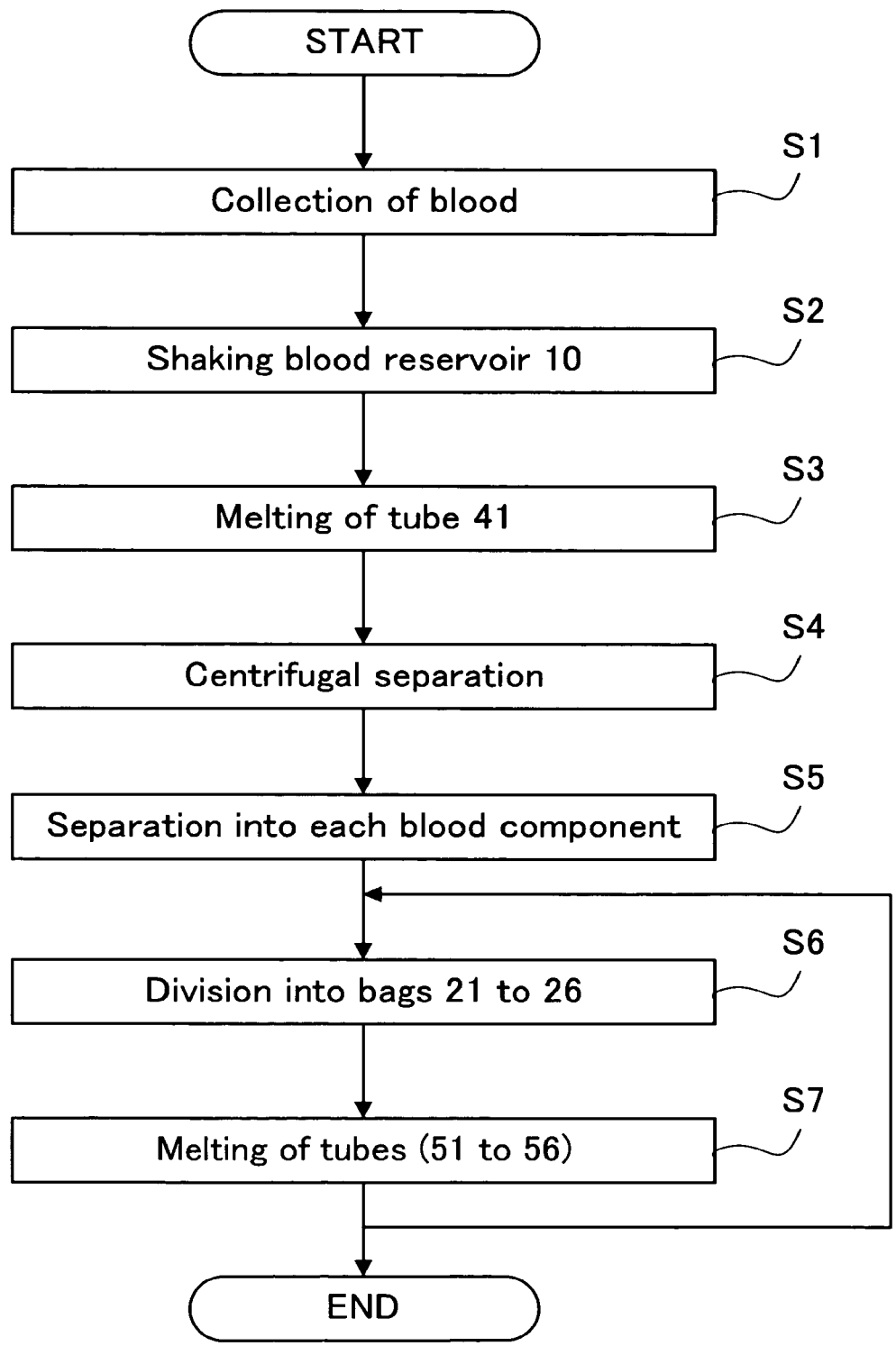
FIG. 2 is a view illustrating a procedure of from collection of the blood to preservation of a serum by the blood component separator according to the first Embodiment of the present invention.

Operation for serum preparation using the blood component separator 1 having the constitution as described above will be explained with reference to FIG. 2 to FIG. 8. FIG. 2 will be referred to freely in combination for explaining the operation.

As shown in FIG. 2, operation for separating blood using the aforementioned blood component separator 1 is constituted from seven steps (S1 to S7) as generally classified.

First, in the first step of the operation, the needle for collecting blood 30 shown in FIG. 1 is stuck into patients, and blood is collected. In this step, the blood collected through the needle for collecting blood 30 is held in the blood reservoir 10 positioned down below via the tube 41 (reservation step S1). A breakable partition wall is mounted between the tube 42 and the blood reservoir 10 such that the collected blood in the blood reservoir 10 does not flow into the component storage part 20. Alternatively, the channel of the tube 42 is closed at the foot side of the blood reservoir 10 using a clamp or the like. The reservation step S1 is terminated after collecting a required amount, taking into account the patient's physical condition upon collecting the blood. The required amount referred to herein may be approximately 200 to 600 ml when there is no problem in the physical constitution and physical condition of the patient.

Upon collecting the blood, a blood collecting device which has been extensively used in blood donation or the like may be also used.

Figure 3:
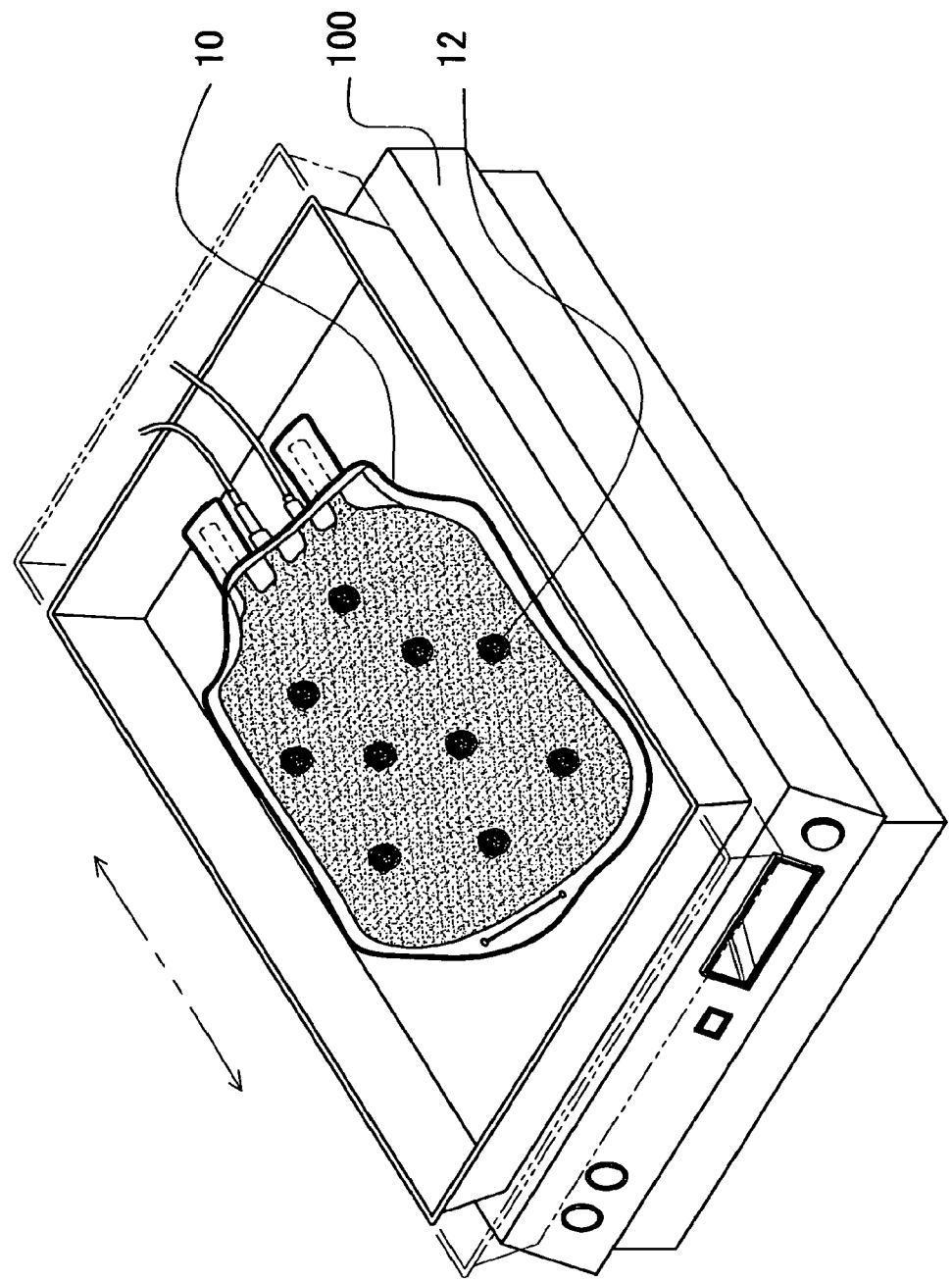
FIG. 3 is a view illustrating a state of shaking a blood reservoir 10 of the blood component separator according to the first Embodiment of the present invention.

Next, as shown in FIG. 2, after initiating the reservation step S1, the blood reservoir 10 is shaken in parallel therewith (activation promoting step S2). As shown in FIG. 3, the blood reservoir 10 reserving the collected blood is gently agitated by a shaking apparatus 100 to be brought into contact with the glass processed bodies 12 stored inside. Then, the platelets and coagulation factors included in the blood are coagulated on the surface of the glass processed body 12, and from the platelets activated during the coagulation are released growth factors derived therefrom. (Also, this activation promoting step carried out at a low temperature is effective in acceleration of platelet agglutination.)

Because the blood reservoir 10 is formed to have the external size that is equivalent to common blood bags, any well known shaking apparatus can be used for shaking the blood reservoir 10. Additionally, although not shown in FIG. 3, the blood reservoir 10 is connected to each of the bags 21 to 26 via each of the tubes 41 to 46 and 51 to 56, and therefore, shaking can be also executed after folding at these connections.

Figure 4:
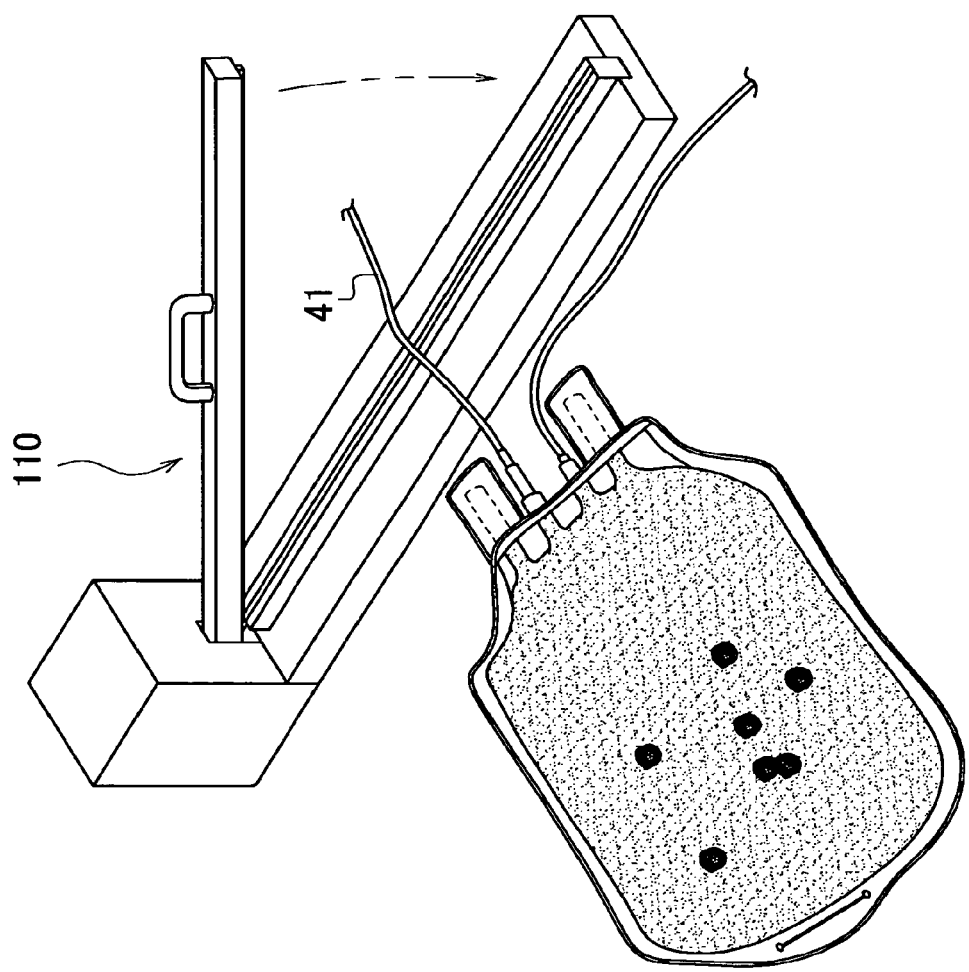
FIG. 4 is a view illustrating a state of melting of a tube 41 of the blood reservoir 10 of the blood component separator according to the first Embodiment of the present invention.

Following the reservation step S1, the needle for collecting blood 30 is drawn to remove from the subject of collection of the blood, and then a part of the tube 41 connecting the needle for collecting blood 30 and the blood reservoir 10 is subjected to melting, and welding of its melting edge (melting step S3) is perfected at the same time. For melting of the tube 41, a melting machine 110 as shown in FIG. 4 (generally referred to as a sealer) can be used to complete melting.

On the other hand, the blood reservoir 10 separated from the patient proceeds through the activation promoting step S2 together with the component storage part 20 and each of the tubes 42 to 46 and 51 to 56 connecting therebetween, as well as branches 61 to 65 and the like. They are taken together to be compact, and are subjected to a centrifuge separation (centrifugal separation step S4). The tube 42 then is kept in the state with the channel being closed by a breakable partition wall or a clamp, similarly to the case of the reservation step S1.

When the blood is collected through adding an anticoagulant previously, the melting step S3 and the centrifugal separation step S4 may be carried out prior to the activation promoting step S2. In this instance, the centrifugal separation may be conducted under the following conditions:

centrifugal separation of whole blood: 4,400 g×4 to 6 min, 2,250 g×10 min; and centrifugal separation of platelet-rich plasma (PRP): 1,100 g×4 to 6 min.

Conditions for centrifugal separation of the blood reservoir 10 may be defined depending on the amount of the reserved blood and type of the components to be separated, however, for example, they may be defined to be, e.g., 2250 g×10 min, at 4° C. With respect to the blood reservoir 10 following the centrifugal separation, explanation will be made with reference to FIG. 5.

Figure 5:
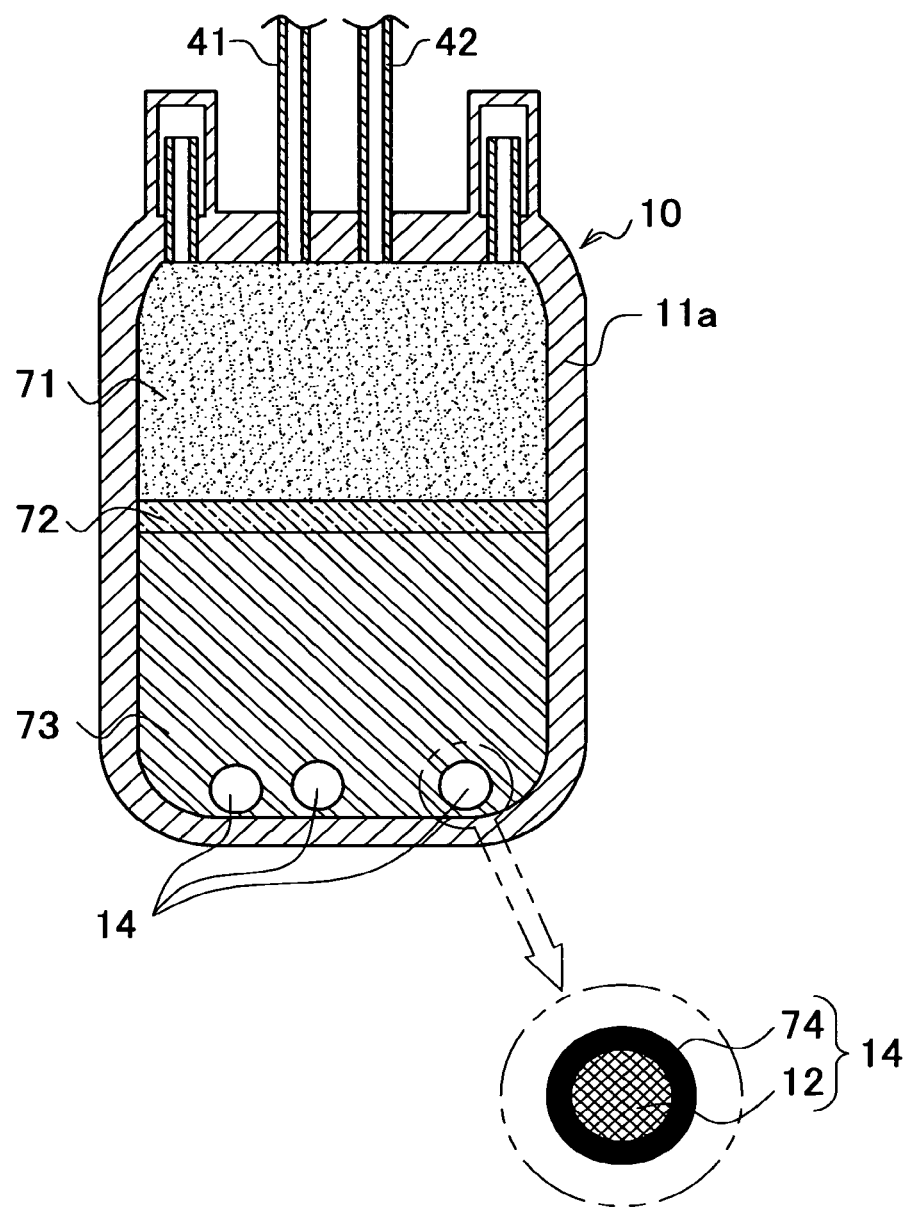
FIG. 5 is a cross sectional view illustrating the blood reservoir 10 after centrifugal separation with the blood component separator according to the first Embodiment of the present invention.

As shown in FIG. 5, in the blood reservoir 10 subjected to the centrifugal separation after proceeding through the activation promoting step S2, the blood is generally separated into three layers of serum 71, leukocytes 72 and erythrocytes 73, although they may vary depending on the centrifugal separation conditions. Additionally, glass processed bodies 12 are lying down in the state with a coagulant 74 of the platelets and coagulation factors adhered on the surface thereof (hereinafter, referred to as "coagulant adhered glass processed body 14") at the bottom of the main body part 11a in the blood reservoir 10. This coagulant adhered glass processed body 14 includes, as shown in the enlarged portion of the Figure, the coagulant 74, which was formed by coagulation of the platelets and coagulation factors, adhered on the surface of the glass processed body 12. In order to discriminate the presence or absence of adherence of the coagulant herein, a reference numeral 14 is assigned to the glass processed body after the adherence of the coagulant 74.

As described above, the serum 71 that is a supernatant component in the state shown in FIG. 5 comprises growth factors derived from the platelets and coagulation factors sufficiently released therefrom in the activation promoting step S2. Also in the centrifugal separation step S4, because both of the two tubes 41 and 42 connected to the upper edge end of the main body part 11 of the blood reservoir 10 in an air-tight manner are kept in a closed state to be inaccessible to the external environment, invasion of microorganisms and the like is prevented.

Referring back to FIG. 2, the factor to be activated, which was activated in the activation promoting step S2 through the centrifugal separation step S4, forms a clot and is separated from the blood (separation step S5).

Furthermore, in the separation step S5, the serum 71 separated and extracted in the blood reservoir 10 is sequentially divided into all or a part of the bags 21 to 26 in the component storage part 20 (discharging step S6). A method for discharging will be explained with reference to FIG. 6.

Figure 6:
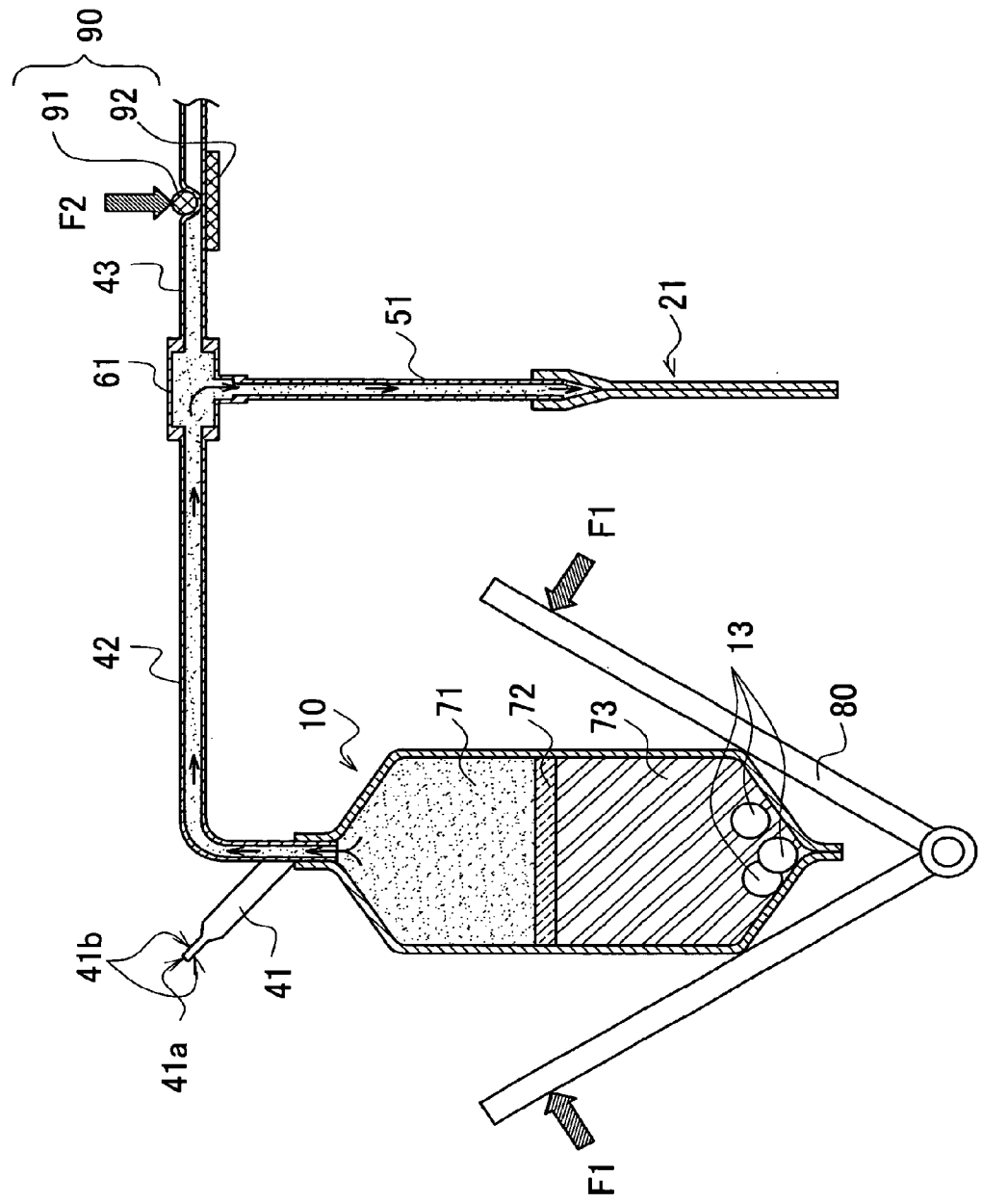
FIG. 6 is a cross sectional view illustrating a method of discharging a serum 71 prepared in the blood reservoir 10 into a bag for preserving serum 21 of the blood component separator according to the first Embodiment of the present invention.

As shown in FIG. 6, when discharge of the extracted serum 71 into the bag 21 of the component storage part 20 is intended, channel of the tube 43 is closed using a clamp 90, and the blood reservoir 10 is compressed (F1) in this state with a pressurizer 80 placed outside of the blood reservoir 10. As described above, the tube 41 connected to the blood reservoir 10 in an air-tight manner is subjected to melting at its midstream 41a when the reservation step S1 is completed, and at the same time, its end and the vicinity 41b are welded.

Hence, a part of the serum 71 that is the supernatant part extracted by the separation is discharged into the bag for preserving serum 21 via the tube 42, the branch 61 and the tube 51 through receiving the compression F1.

Closure of the channel of the tube 43 can be performed by pinching the flexible tube 43 between a circular disc 91 and a base 92 of the clamp 90.

Figure 7:
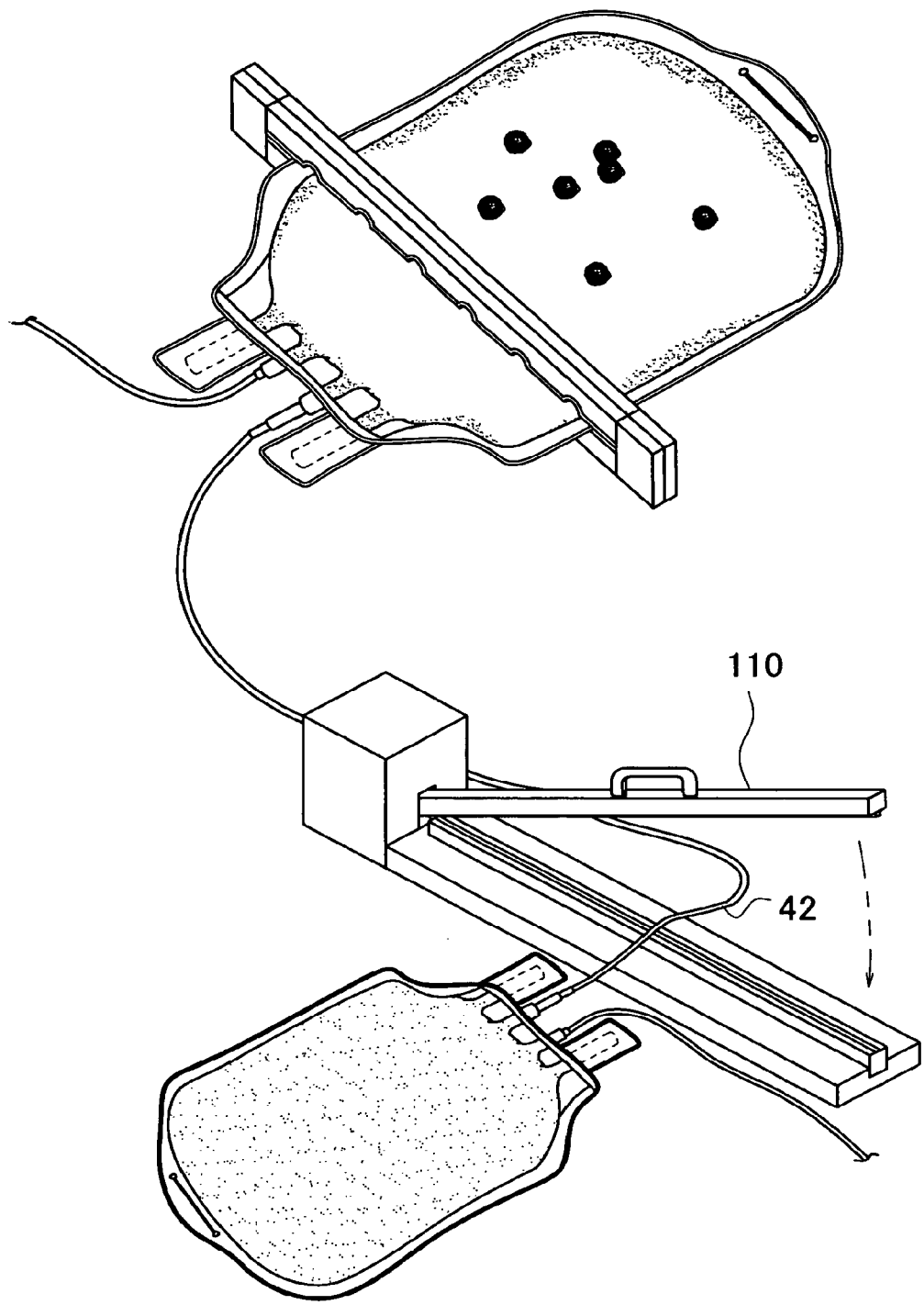
FIG. 7 is a view illustrating a state of melting of a tube 42 of the bag and the blood reservoir 10 of the blood component separator according to the first Embodiment of the present invention.
Figure 8:
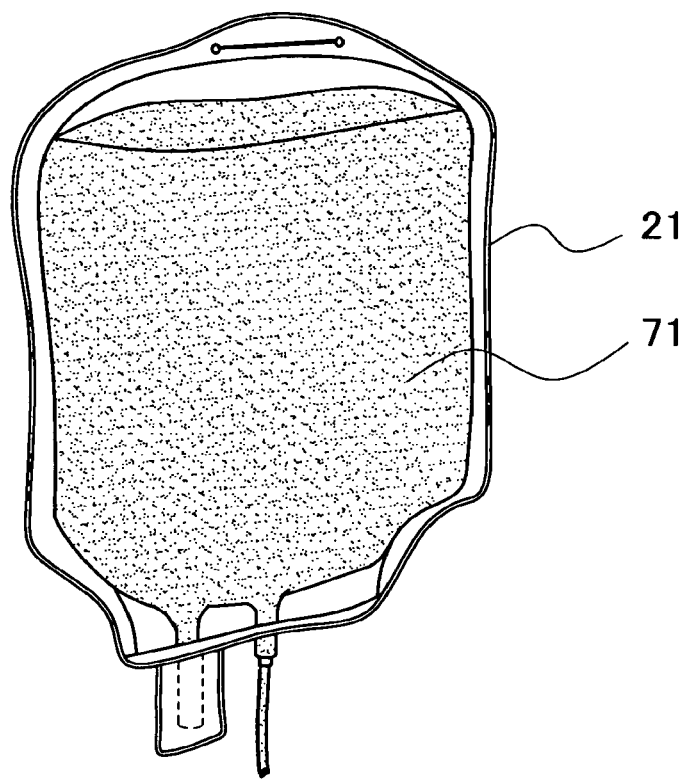
FIG. 8 is a view illustrating a bag 21 following the melting step in the blood component separator according to the first Embodiment of the present invention.

Referring back to FIG. 2, after packing the bag 21 with the serum 71 in a required amount, the tube 51 is subjected to melting and welding (melting step S7). This melting and welding may be performed using a method that is similar to melting and welding of the tube 42 prior to the aforementioned centrifugal separation step S4, as shown in FIG. 7. Moreover, as shown in FIG. 8, the bag 21 including the serum 71 packed therein is subjected to a preservation treatment such as, e.g., freezing preservation.

This discharging step S6 and melting step S7 is sequentially carried out on each of the bags 21 to 26, and the operation for serum preparation is terminated when the serum 71 is packed in all or a part of the bags 21 to 26. Additionally, as needed, the erythrocytes 73 may be washed and diluted with an anticoagulant such as physiological saline solution, CPD, or an ACD-A solution, or solution for preserving blood such as MAP, and can be preserved as blood for transfusion. This method will be described later.

Significance of Blood Component Separator 1

In the blood component separator 1 according to this Embodiment, the blood reservoir 10 is constituted from the main body part 11 having an internal volume that is equivalent to the blood bags, and the glass processed bodies 12 are provided inside thereof. Because the serum is prepared in this blood reservoir 10 from the blood, a larger amount of serum can be prepared at a time in comparison with cases in which a conventional blood collection tube is used, thereby accomplishing advantages in light of steps in the preparative operation, and the like. Furthermore, this may reduce risk of contamination of the prepared serum with microorganisms and the like, and therefore, the blood component separator 1 is also suited for preparing a serum having high safety.

Additionally, because the glass processed bodies 12 are stored as a blood coagulation accelerating substance in the blood component separator 1, adherence of the clot onto the surface of the glass processed body 12 in preparation of the serum, and contamination with fibrin and clot in the serum during fractionation of the serum can be prevented.

Moreover, in the blood component separator 1, in addition to the aforementioned advantages, the blood or the serum is not exposed to the external environment because the blood reservoir 10, and the bags 21 to 26 and each of the tubes 41, 42, and 51 to 56 are connected in an air-tight manner to make the inner space inaccessible to the external environment. Thus, even higher safety is ensured.

Furthermore, because the aforementioned tubes 41, 42, and 51 to 56 have flexibility, and are formed with a material that permits melting and welding, the inside thereof is not exposed to the external environment when these channels are cut off in a timely manner. Therefore, also in this respect, the blood component separator 1 can be referred to as having high safety.

In general, when blood is held in a container not including any anticoagulant (for example, ACD-A liquid or the like), platelets and coagulation factors in the blood gradually coagulate after leaving the container to stand for 20 minutes or longer after collection of the blood. However, when the amount of the air in the container is small, in particular, coagulation of the blood is not accelerated, thereby causing the problem of requirement of a long period of time until coagulation is accomplished.

In contrast, in the blood component separator 1 according to this Embodiment, because glass processed bodies 12 as a blood coagulation accelerating substance having a blood coagulation accelerating function are disposed inside the blood reservoir 10 for holding the blood, most platelets (for example, 95% or more of the platelets) and coagulation factors are caused to coagulate within 10 minutes, thereby enabling operation of the serum preparation to be quickly performed. Accordingly, when the blood component separator 1 according to this Embodiment is used, the serum can be quickly prepared. Furthermore, because erythrocytes remaining in the blood component separator 1 after preparing the serum via the aforementioned activation promoting step S2 scarcely form clot, there is a possibility of reuse of the erythrocytes as a component for blood transfusion.

Moreover, in the field of regenerative medicine, for example, serums having high safety are required for culturing stem cells. A large amount of serum can be prepared and preserved in a safe and quick manner by preparation and preservation of the serum 71 using the blood component separator 1 as described above. Accordingly, when the blood component separator 1 according to this Embodiment is used, regeneration therapy for a tissue or a function can be performed with high efficiency on a patient while securing high safety.

Also, in the above Embodiment, activation of platelets and coagulation factors in the blood can be further promoted when the glass processed body 12 was defined to have a surface area so as to satisfy a relationship of from 0.1 $mm^2$/ml or greater in the volume of the blood which can be reserved in the blood reservoir 10. Moreover, when the surface area of the glass processed body 12 in the volume of reservable blood is defined to fall within the range of from 0.1 $mm^2$/ml to 25 $mm^2$/ml, simultaneous achievement of both suppression of hemolysis in the activation promoting step S2 and the centrifugal separation step S4, and promotion of activation of the platelets and coagulation factors may be enabled.

Number of the glass processed bodies 12 in the blood reservoir 10 was specified to be three in this Embodiment, but this is not limited thereto. The number of stored glass processed bodies 12 may be from 1 to 50 from a practical point of view.

Moreover, although glass processed bodies 12 were used as a blood coagulation accelerating substance in the blood component separator 1, the blood coagulation accelerating substance is not limited thereto. For example, any one that constitutes the contact region with the blood with an inorganic substance consisting of at least one selected from silicon dioxide compounds such as silica, diatomaceous earth and kaolin may be also used. Furthermore, the substance provided at the contact region is not limited to an inorganic substance.

Additionally, the blood coagulation accelerating function was imparted to the blood reservoir 10 by storing the blood coagulation accelerating substance (glass processed body 12) having a blood coagulation accelerating function in the blood reservoir 10 according to the aforementioned blood component separator 1; however, any constitution is permitted as long as the blood coagulation accelerating function is achieved even though a blood coagulation accelerating substance is not necessarily stored in the blood reservoir 10. For example, a part of the inside wall in the main body part 11 of the blood reservoir 10 may be covered by the aforementioned inorganic substance or the like.

Furthermore, the shape of the glass processed body 12 in the blood component separator 1 was made substantially spherical; however, the shape of the blood coagulation accelerating substance according to the present invention is not limited thereto. However, with respect to reduction of occurrence of hemolysis and breakage of the bag and the like upon centrifugal separation or the like, the outer surface (contact region with the blood) is preferably formed to give a continuous curved face.

Figure 9:
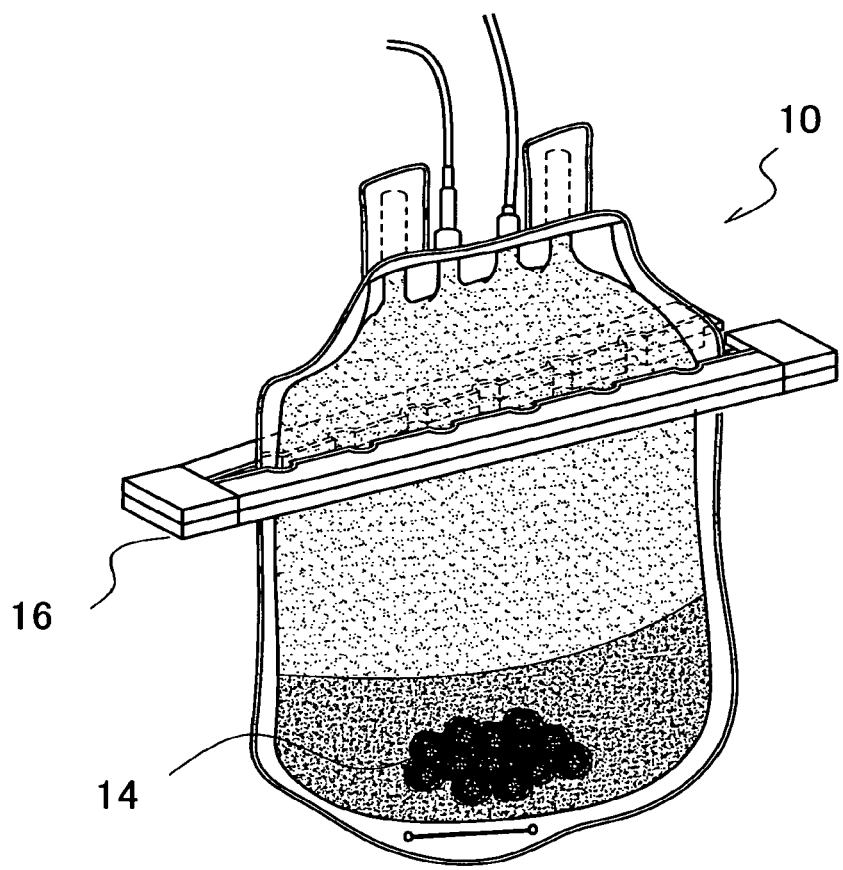
FIG. 9 is a perspective view illustrating the blood reservoir 10 in the discharging step following centrifugal separation of the blood component separator according to the first Embodiment of the present invention.

In the discharging step S6, as shown in FIG. 9, the erythrocytes can be discharged through blocking the glass processed bodies, to which fibrin was adhered, with a holding part 16 such as, for example, a clamp from the outside of the blood reservoir 10 to separate the glass processed bodies including the platelets and coagulation factors adhered onto the surface thereof. This holding part 16 preferably has a face with a wave form or an uneven shape to be in contact with the blood reservoir 10 so that washing fluids of erythrocytes and fibrin and the like can be passed through even after pinching the blood reservoir 10.

Furthermore, although solid glass processed body 12 was used in the Embodiment of the present invention, it may not be necessarily solid as long as a substance having a blood coagulation accelerating function is formed on its outer surface. For example, it may have a porous structure, and the entire region to be in contact with the blood including the wall face in the pores may be coated with a silicon dioxide compound such as glass.

Second Embodiment

The blood component separator according to this Embodiment has a difference with the aforementioned blood component separator 1 according to the first Embodiment, in the mode of the glass processed body stored in the blood reservoir 10. Thus, the mode of the glass processed body will be explained below with reference to FIG. 10, although description of other parts will be omitted.

Figure 10:
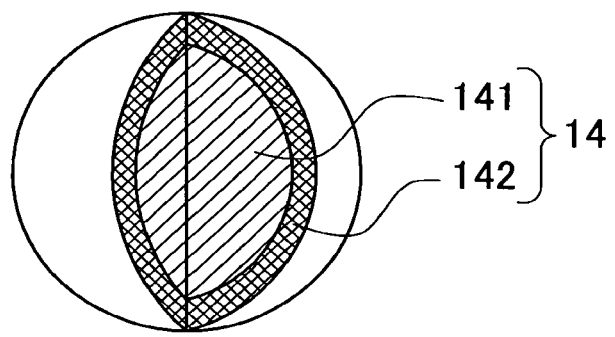
FIG. 10 is a perspective view (partial cross sectional view) illustrating a coagulant adhered glass processed body 14 according to the blood component separator according to a second Embodiment of the present invention.

As shown in FIG. 10, the coagulant adhered glass processed body 14 according to this Embodiment is similar to the glass processed body 12 described above in terms of having a shape which is substantially spherical; however, it is characterized in having a two-layered structure including a core body part 141 and a superficial part 142.

Among the two layers constituting the coagulant adhered glass processed body 14, the core body part 141 is constituted with a magnet. On the other hand, the superficial part 142 is constituted with, for example, soda glass, as an inorganic substance that is identical to the material constituting the aforementioned glass processed body 12.

When the blood reservoir 10 storing therein the coagulant adhered glass processed bodies 14 having such a structure is used, an effect to facilitate stirring of the blood can be achieved by allowing a magnetic field to act on the blood reservoir 10 while shaking in the activation promoting step S2 shown in FIG. 2. More specifically, by allowing a magnetic field to act on the blood reservoir 10 from outside with, for example, a stirrer such as a magnetic stirrer, rotary movements of the coagulant adhered glass processed bodies 14 are caused in the container to result in contact with the blood with higher efficiency.

Therefore, in the blood component separator having the coagulant adhered glass processed bodies 14 in the blood reservoir 10, activation of the platelets and coagulation factors can be more rapidly perfected than the aforementioned blood component separator 1, thereby enabling quicker preparation of the serum.

Additionally, when the glass processed bodies 14 are constituted with a magnet, they can be fixed with a magnet from outside of the blood reservoir 10 in the discharging step S6.

Third Embodiment

The blood component separator according to this Embodiment has a difference with the aforementioned blood component separator 1 according to the first Embodiment, in that one of the bags 21 to 26 constituting the component storage part 20 is provided for use to let air away (see FIG. 1). Upon collection of blood, the air is inevitably included in the blood reservoir 10 in a volume under the capacity of the tube 41; however, presence of less air is preferred in the separation step in each blood component S5. Hence, when a bag to let air away according to this Embodiment is provided between the blood reservoir 10 and the component storage part 20, the air alone can be removed prior to the separation step into each blood component S5. Other constitutions in this Embodiment are similar to that in the first Embodiment, and therefore, description of other parts is omitted.

Fourth Embodiment

Figure 11:
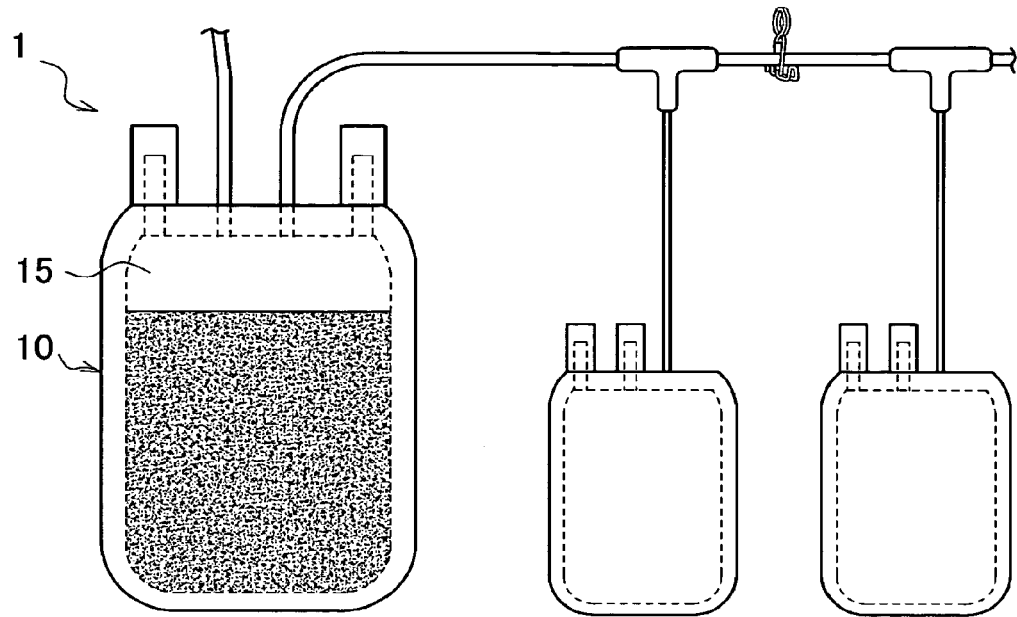
FIG. 11 is a view illustrating a blood component separator 1 according to a fourth Embodiment of the present invention.

The blood component separator according to this Embodiment has a difference with the aforementioned blood component separator 1 according to the first Embodiment, in the inclusion of the air 15 in place of the blood coagulation accelerating substance added to the blood reservoir 10, as shown in FIG. 11. In this case, because there is no need to previously add the blood coagulation accelerating substance, reduction of manufacturing cost may be accomplished. Content of the air 15 is preferably from 0.03 cc/ml to 1 cc/ml per the volume of the reservable blood. It is preferred that the tube 41 have a mechanism for preventing leakage of the air included to give the aforementioned content, until the time of use.

Also, the air and the blood coagulation accelerating substance may be used in combination.

Fifth Embodiment

Figure 12:
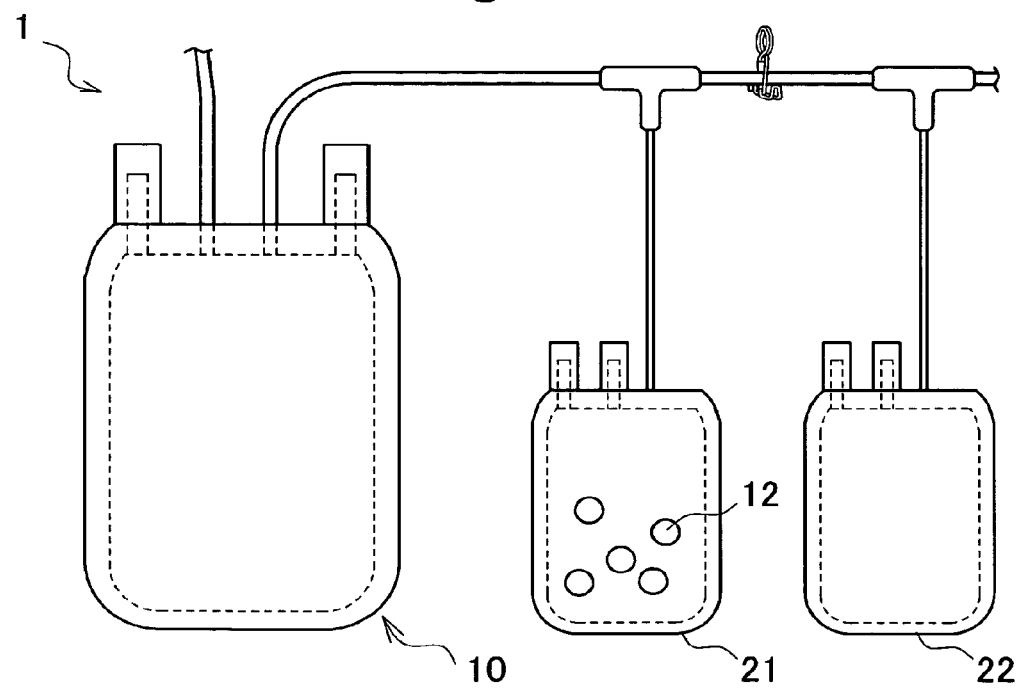
FIG. 12 is a view illustrating a blood component separator 1 according to a fifth Embodiment of the present invention.

The blood component separator according to this Embodiment has a difference with the aforementioned blood component separator 1 according to the first Embodiment, in addition to the glass processed bodies 12 (blood coagulation accelerating substance) to at least one of the bags 21 to 26 constituting the component storage part of the blood component separator 1, as shown in FIG. 12. Moreover, in the case of this Embodiment, a citric acid neutralizing agent including calcium ions may be further added to the container to which the glass processed bodies 12 are added. In this instance, so-called "blood bag for donation" to which an anticoagulant such as a CPD solution is added can be used as the blood reservoir 10.

The blood in the blood reservoir 10 can be separated to some extent by centrifugal separation or the like, but the serum cannot be produced without modification because the anticoagulant was added. In this Embodiment, the blood in the blood reservoir 10 is neutralized with the neutralizing agent added to the bag 21. Thus, the growth factors in the blood are activated, thereby enabling the produced serum to be discharged into the bag 22.

Sixth Embodiment

Figure 13:
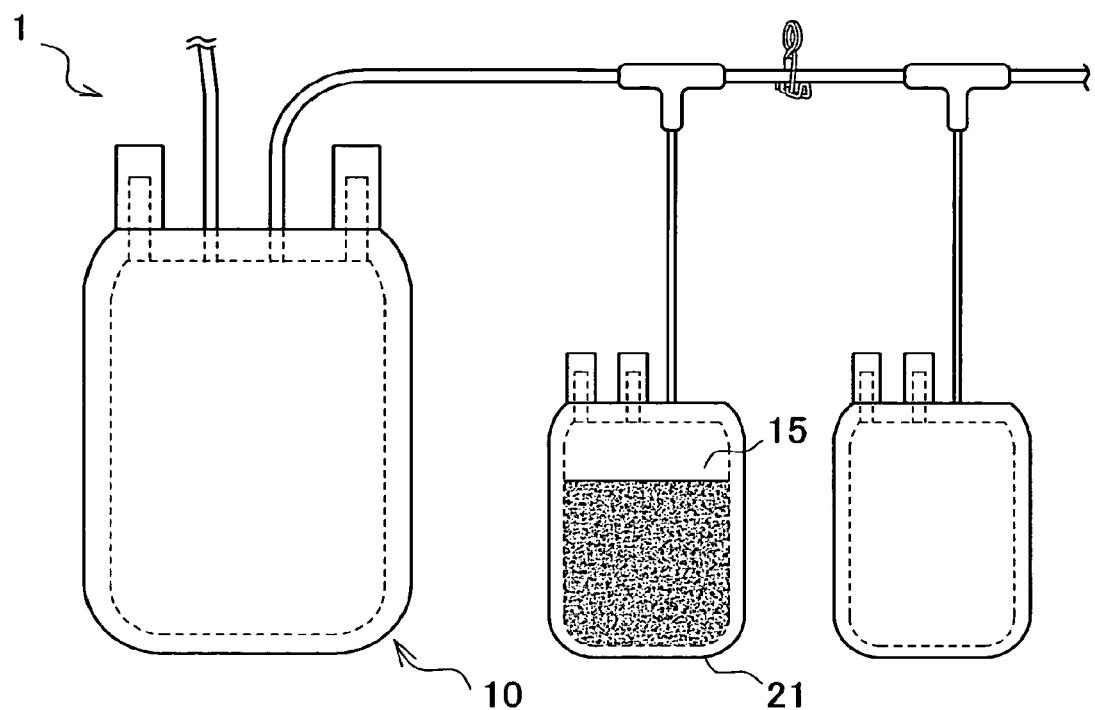
FIG. 13 is a view illustrating a blood component separator 1 according to a sixth Embodiment of the present invention.

The blood component separator according to this Embodiment has a difference with that according to the fifth Embodiment, in the inclusion of the air 15 in place of the blood coagulation accelerating substance added to the bag 21 of the blood component separator 1, as shown in FIG. 13. In this case, similarly to the fourth Embodiment, reduction of manufacturing cost may be accomplished because there is no need to previously add the blood coagulation accelerating substance. Content of the air 15 is preferably from 0.03 cc/ml to 1 cc/ml per volume of the held blood. It is preferred that the tube 51 have a mechanism for preventing leakage of the air included to give the aforementioned content, until the time of use.

Also, the air and the blood coagulation accelerating substance may be used in combination.

Moreover, the blood component separator 1 according to the first Embodiment and the fourth Embodiment has a component storage part constituted from six bags 21 to 26, however, number of the bags constituting the component storage part is not limited thereto. In addition, although glass processed bodies are used as the blood coagulation accelerating substance in the blood component separator 1 according to the first Embodiment and the fourth Embodiment, similar effect may be also achieved when the air is include in place of the glass processed body.

In this instance, it is preferred to give from 0.03 cc/ml to 1 cc/ml per the volume of the reservable blood.

Also, according to the present invention, effective utilization of erythrocytes and fibrin remaining in the blood reservoir 10 following separation of the blood is enabled. Hereinafter, such modes will be explained in detail.

Seventh Embodiment

Figure 14:
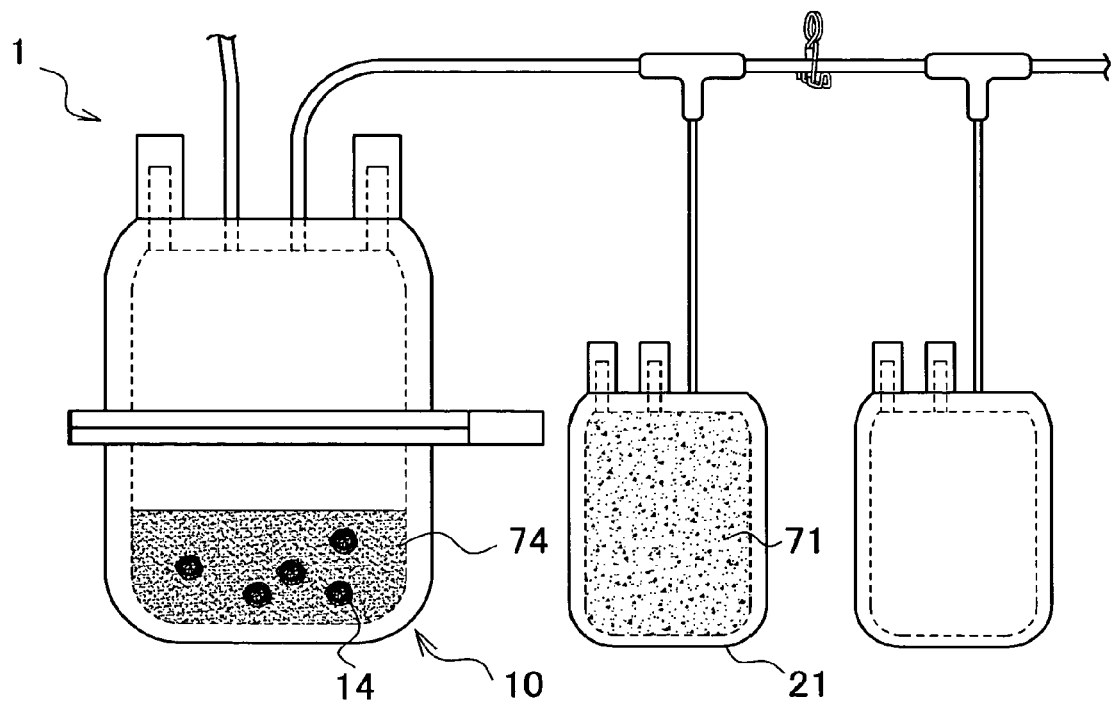
FIG. 14 is a view illustrating a blood component separator 1 according to a seventh Embodiment of the present invention.
Figure 15:
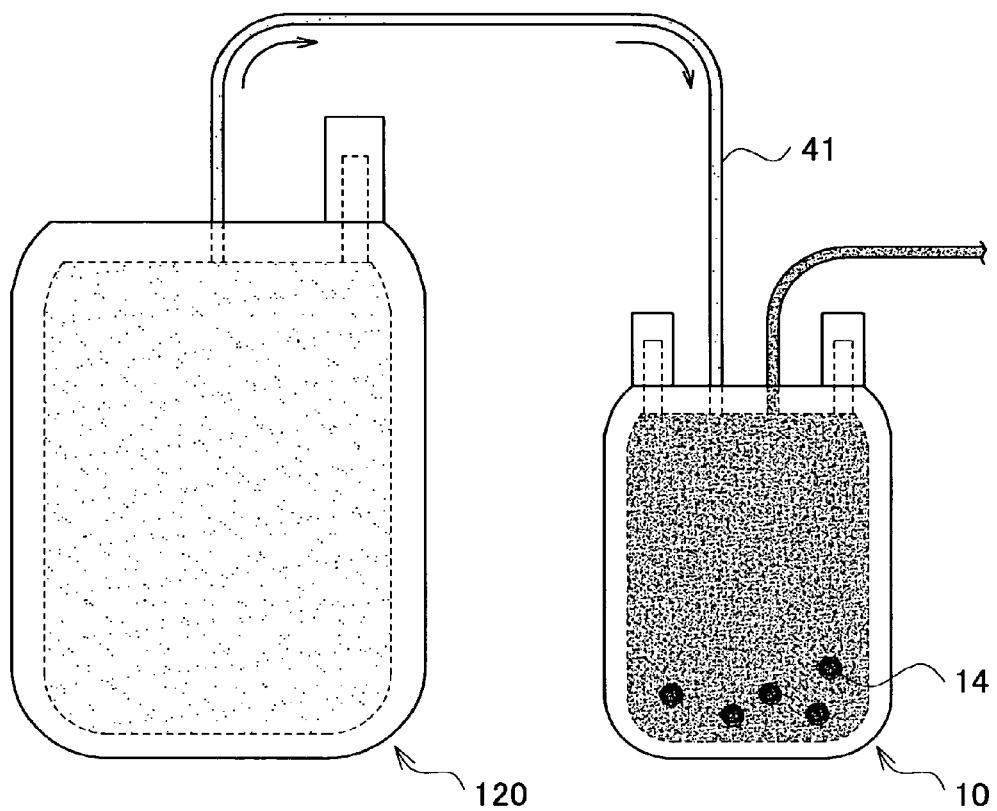
FIG. 15 is a view illustrating a step of introducing physiological saline solution into a blood reservoir 10 of the blood component separator 1 according to the fifth Embodiment of the present invention.

The blood component separator 1 which separated the blood in the first Embodiment is used. As shown in FIG. 14, the blood reservoir 10 after separating the blood and discharging the serum into the bag 21 (component storage part) includes the coagulant adhered glass processed bodies 14 to which fibrin is adhered and residues of erythrocytes, and the like. Physiological saline may be previously charged in any one in which the serum was not stored, among the component storage parts 21 to 26 connected to this blood reservoir 10 in an air-tight manner, alternatively, a physiological saline-containing bag 120 which contains physiological saline is connected to the tube 41 of this blood reservoir 10 to allow for mixing with the erythrocytes in the blood reservoir 10. Accordingly, the mixture can be used as blood for transfusion (see FIG. 15). Furthermore, the coagulant adhered glass processed bodies 14 to which fibrin was adhered may be additionally washed after discharging all blood components, and the resulting fibrin obtained after washing can be used as a scaffold of stem cells or as a barrier for wounds.

Moreover, a constitution involving the blood reservoir and the component storage part being communicated with a tube therebetween was adopted as a blood component separator in the first Embodiment and the second Embodiment; however, the part for reserving the blood and the part for reserving the serum are not necessarily constituted as distinct containers. For example, one container constituted such that a part thereof can be cut away by melting, welding or the like is provided, and the blood is held in this container, thereby providing a constitution which may be used as a component storage part 20 therefrom. In addition, a clamp which pinches the blood reservoir 10 such that the glass processed bodies 12 to which fibrin was adhered, or the coagulant adhered glass processed bodies 14 are not discharged was demonstrated in the discharging step S6, but is not limited thereto.

Eighth Embodiment

Figure 24:
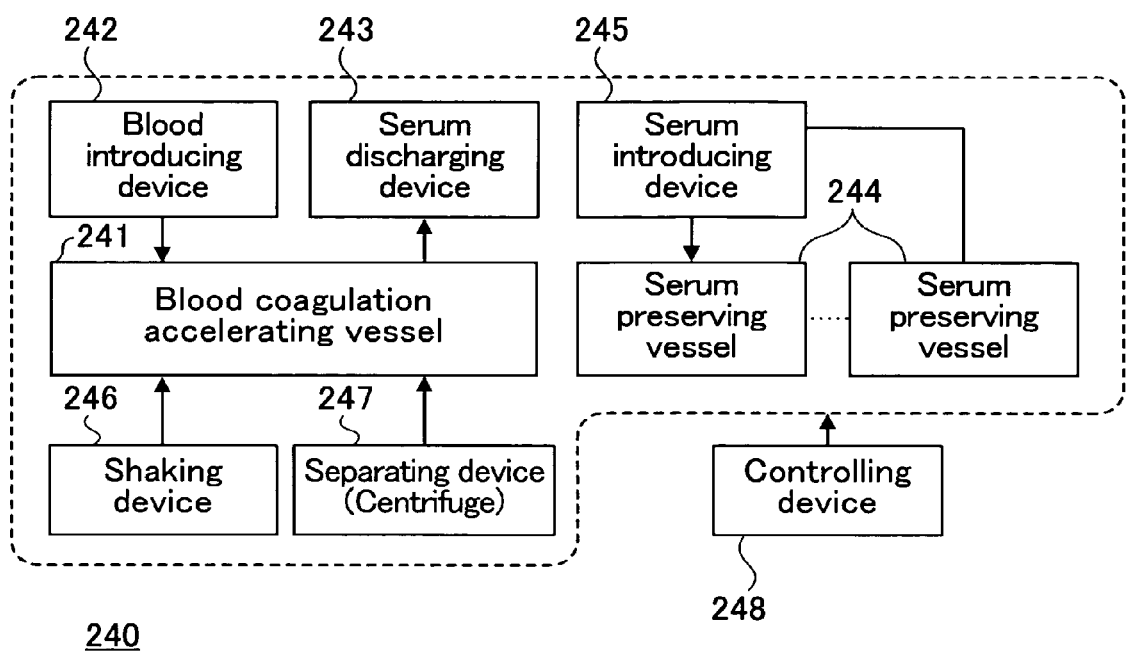
FIG. 24 is a functional block diagram illustrating a constitution of the serum preparation apparatus according to an eighth Embodiment.

Execution of mechanical and automatic serum preparation and serum division as explained in the above Embodiments is enabled by the serum preparation apparatus of this Embodiment. As shown in FIG. 24, the present serum preparation apparatus 240 is constituted from a blood introducing device 242 (head pressure, ejection pump or the like) for aseptically introducing the collected blood to a blood coagulation accelerating container 241, a serum discharging device 243 (suction pump or the like) for aseptically discharging the serum prepared by the blood coagulation accelerating container, a serum introducing device 245 (head pressure, ejection pump or the like) for discharging and/or distributing the discharged serum into a plurality of serum preserving containers 244, a shaking device 246 for shaking the container for preparing serum since initiation of introduction of the blood to the container for preparing serum, a separating device 247 for separating serum components by centrifugal separation of the container for preparing serum after completing shaking, and a controlling device 248 for controlling each operation timing and operation itself. The blood coagulation accelerating container is a container having a blood coagulating function for the purpose of preparing a serum as described above, which may be any container having a blood coagulating function such as one including a glass processed body in a flexible bag as described above, as well as a glass container or the like. Also, a container having mixing/charging ports 511 to 516 shown in FIG. 30 may be used. In order to maintain sterility, a structure for making the handled liquid inaccessible to the outside air may be provided so that contamination of the liquid with microsomes can be avoided, but the form thereof is not particularly limited. Also, the amount of the liquid such as blood, serum or the like as described above may be monitored by a known flowmeter, and the operation may be controlled (control of the amount of introduced blood, control of the amount of distribution of the serum and the like) based on the results of the same. Moreover, following distribution of the serum, the serum preserving container may be automatically sealed hermetically.

According to the aforementioned serum preparation apparatus 240, the serum is automatically prepared after collecting the blood, and the prepared serum is automatically distributed into the preservation container. Therefore, preparation of the serum can be extremely easily carried out.

When the preparation container is separately attached after preparing the serum in the aforementioned serum preparation apparatus 240, it may serve as a distribution apparatus so that distribution into the preservation container can be effected.

Ninth Embodiment

Figure 25:
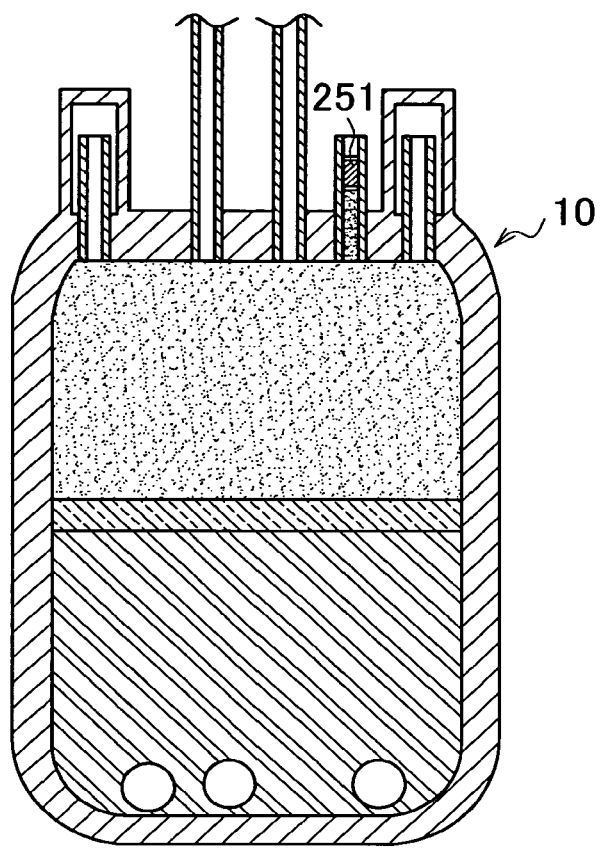
FIG. 25 is a schematic view illustrating a constitution of a flexible bag according to a ninth Embodiment.

FIG. 25 shows a flexible bag (container corresponding to 10 in FIG. 1) having a filter 251 for regulating the quantity of the air in a serum preparation bag.

The filter has a function to regulate the quantity of the air through making the filter open to the outside (opened by opening the cover, not shown in the Figure) after introducing the blood into the bag. The filter is provided to avoid the inability of recovering a blood component such as erythrocytes through generation of clot due to insufficient performance of stirring when the quantity of the air is too great. Thus, a function to regulate blood coagulation velocity to be a relatively suitable value for the amount of the blood is provided by regulating the quantity of the air.

Tenth Embodiment

Figure 26:
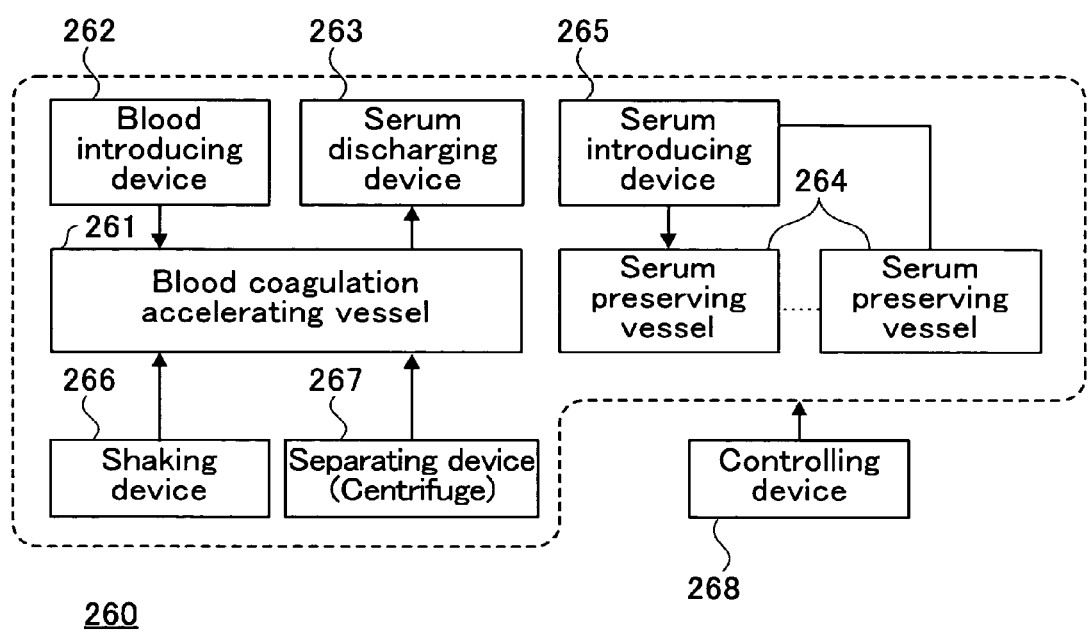
FIG. 26 is a functional block diagram illustrating a constitution of the serum preparation apparatus according to a tenth Embodiment.

FIG. 26 is a functional block diagram of the serum preparation apparatus having a function of regulating the time when the blood coagulation accelerating container 261 is shaken for preparing the serum such that the amount of serum preparation is optimized to attain a sufficient level.

Although the constitution is similar to the apparatus shown in FIG. 24, control of shaking is executed in which the shaking time period is defined to be a continuing predetermined time from the time point of initiation of introducing the blood into the container for preparing serum, up to following termination of collecting the blood. Accordingly, the serum is efficiently produced. This is an operation control which was realized on the basis of the inventor's empirical rule that the serum can be sufficiently produced by starting shaking from the time point of initiation of the collection of the blood, and shaking for a time period longer than the time period of the collection of the blood. The shaking time may be also determined on the basis of results of monitoring of the amount of the serum produced in effect.

Eleventh Embodiment

In this Embodiment, cases in which the serum prepared without using hemocyte components is predominantly used are assumed. This Embodiment is characterized by the container for preparing serum in which a serum separating agent is stored in addition to the aforementioned glass processed body. By including the serum separating agent in this manner, production of the serum can be facilitated through acceleration of blood coagulation by the glass. Thus, the produced serum can be separated from other components well and efficiently.

Twelfth Embodiment

Figure 27:
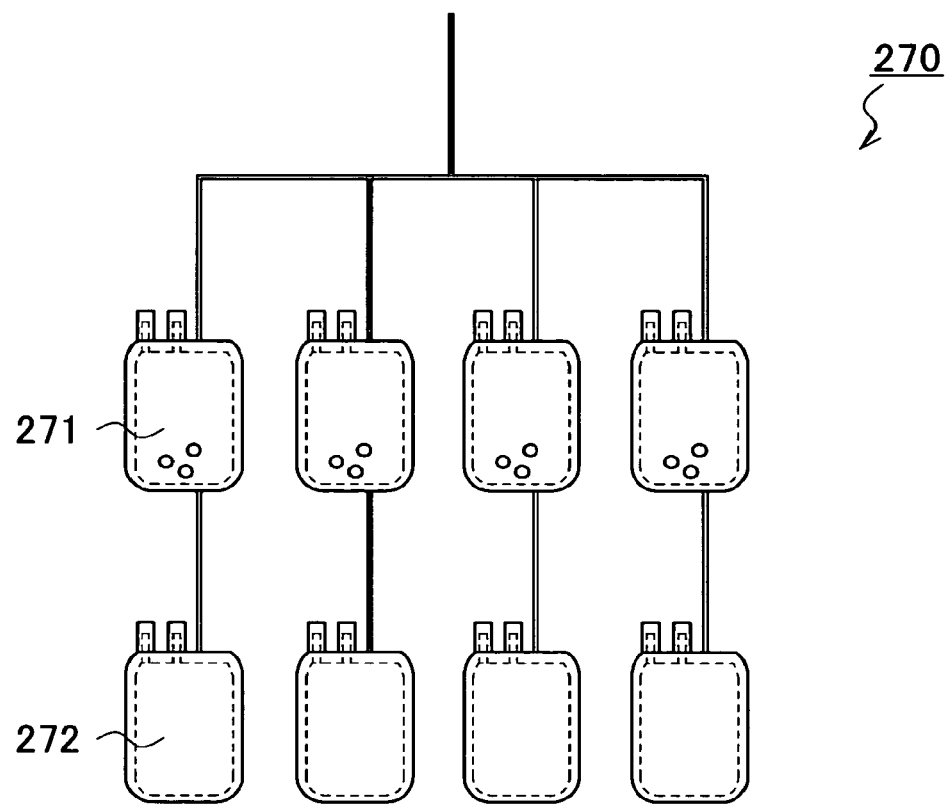
FIG. 27 is a schematic view illustrating a constitution of the serum preparation apparatus according to a twelfth Embodiment.

FIG. 27 shows a serum preparation apparatus 270 that is an apparatus for preparing a serum in which acceleration of blood coagulation is permitted from the collected blood, similarly to the serum preparation apparatus shown in FIG. 1. Differences between the serum preparation apparatus 270 and that shown in FIG. 1 lie in distribution of the collected blood into a plurality of containers for preparing serum 271, preparation of the serum in the container for preparing serum 271, and transfer and/or preservation of the prepared serum in a plurality of preservation containers 272. By thus distributing the collected blood into a plurality of containers for preparing serum 271 and preparing the serum in the container for preparing serum 271, the container for preparing serum is more expanded, resulting in greater degree of freedom of the glass processed body. Accordingly, stirring of the glass is facilitated to improve accessibility to the blood, thereby enabling carrying out more efficient preparation of the serum.

Thirteenth Embodiment

Figure 28:
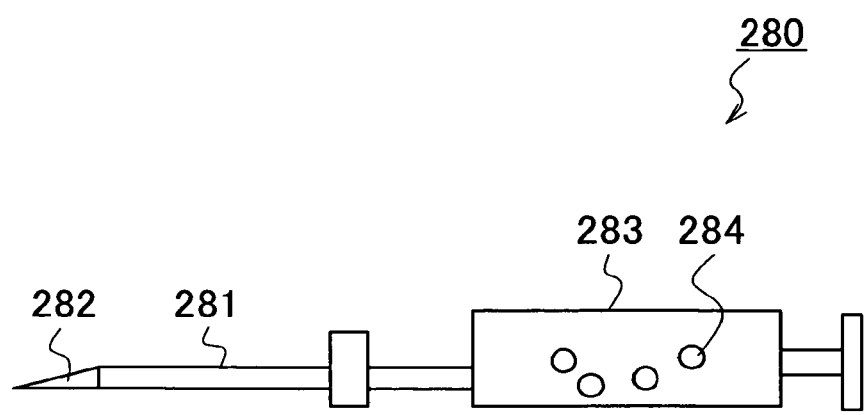
FIG. 28 is a schematic view illustrating a constitution of the serum preparation apparatus according to a thirteenth Embodiment.

FIG. 28 shows a novel serum preparation apparatus 280. The serum preparation apparatus 280 has an indwelling needle 282 connected to a catheter 281, and a syringe 283 connected to the end of the catheter 281, with the syringe 283 including a blood coagulation accelerating substance 284 (glass or the like) stored therein.

According to the aforementioned serum preparation apparatus 280, preparation of the serum is enabled by introducing the collected blood into the syringe 283 through the catheter 281 from the indwelling needle 282 while shaking the syringe 283. Thereafter, the serum can be separated by centrifugation of the whole syringe 283. When a serum is prepared from a human body with this serum preparation apparatus 280, the operation is preferably conducted as far as possible from the human body while positioning the syringe 283 down below the site of collection of the blood such that coagulation signal of the blood coagulation is not transmitted to the human body.

Fourteenth Embodiment

Figure 29:
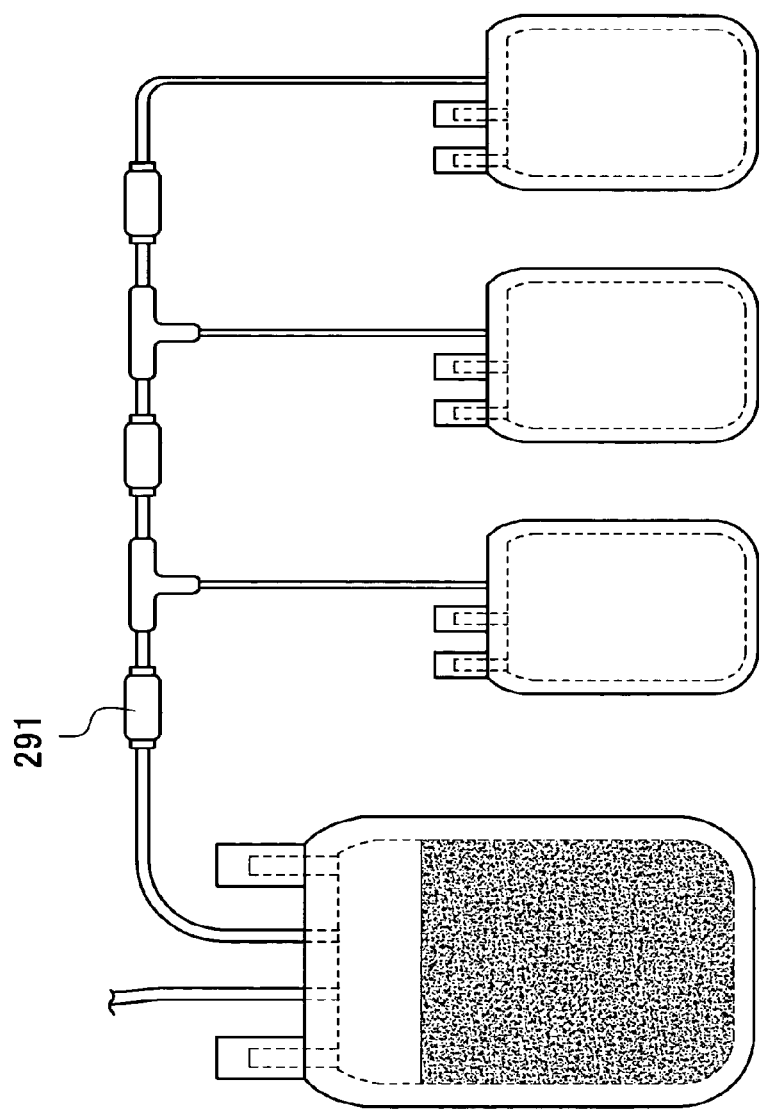
FIG. 29 is a schematic view illustrating a constitution of the serum preparation apparatus according to a fourteenth Embodiment.

FIG. 29 shows a constitution that is substantially similar to the serum preparation apparatus shown in FIG. 1, but is greatly different in that a filter 291 is provided in a communicating path between the bag and the bag. This filter 291 is a filter having a pore with a size capable of selectively passing the serum without passing the hemocyte components. Consequently, the serum can be conveniently separated by passing the liquid after shaking through this filter even though the centrifugal separation step is not conducted.

Fifteenth Embodiment

Figure 30:
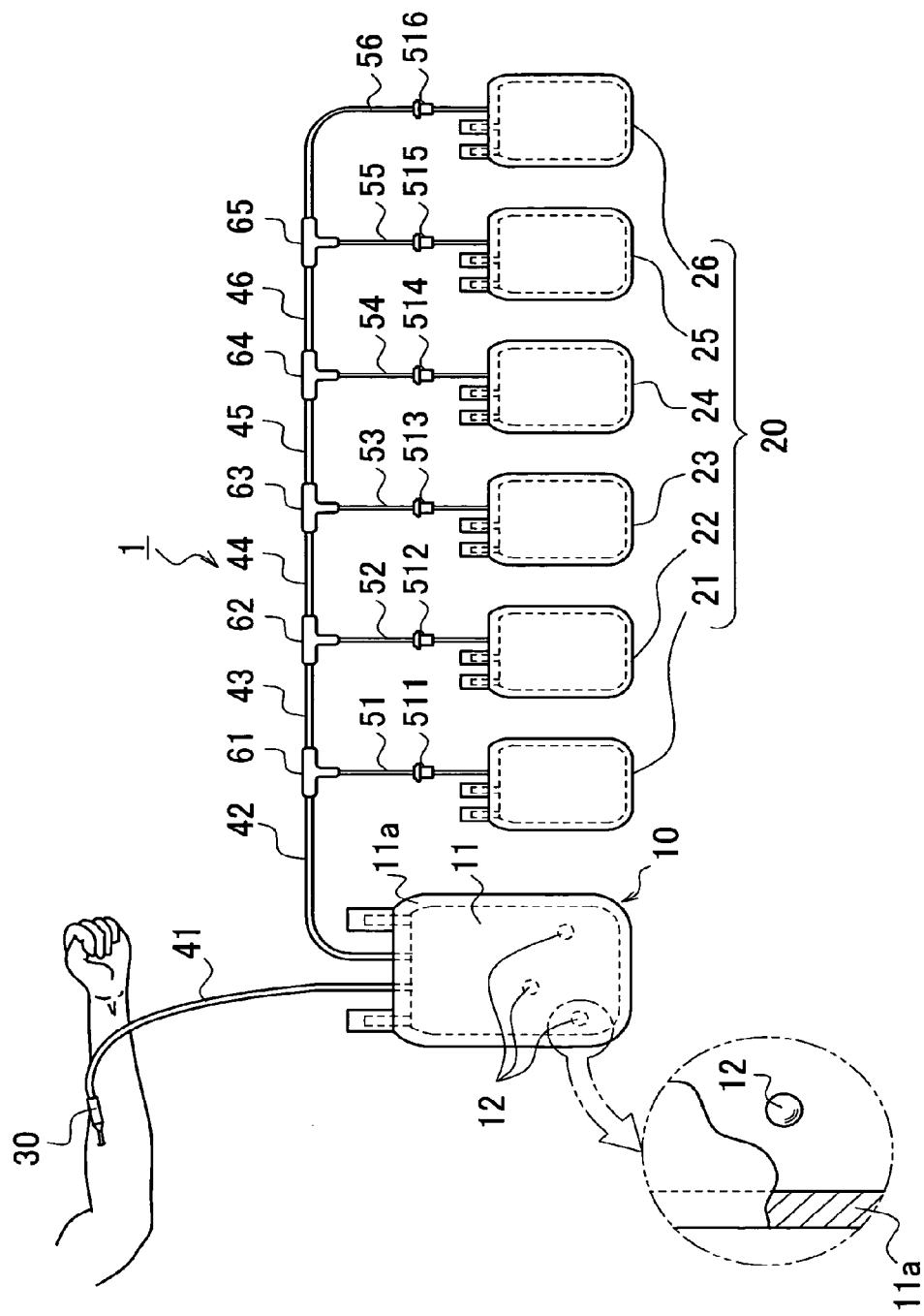
FIG. 30 is a schematic view illustrating a constitution of the serum preparation apparatus according to a fifteenth Embodiment.

FIG. 30 shows a constitution that is substantially similar to the serum preparation apparatus shown in FIG. 1, but is different in that it is a serum preparation apparatus having each bag constituted in an aseptically connectable and detachable manner. Exemplary constitution in a connectable and detachable manner includes a constitution having a highly air-tight mixing/charging port with a function to allow opening/closing of a slit type opening of a valve with attachment/detachment of an insertion instrument (see, Japanese Patent No. 3389983). In this case, a luer is desirably used at the tip of the tube as a communicating path to be connected. According to such a constitution, attachment and detachment of the bag can be readily carried out.

Sixteenth Embodiment

Figure 31:
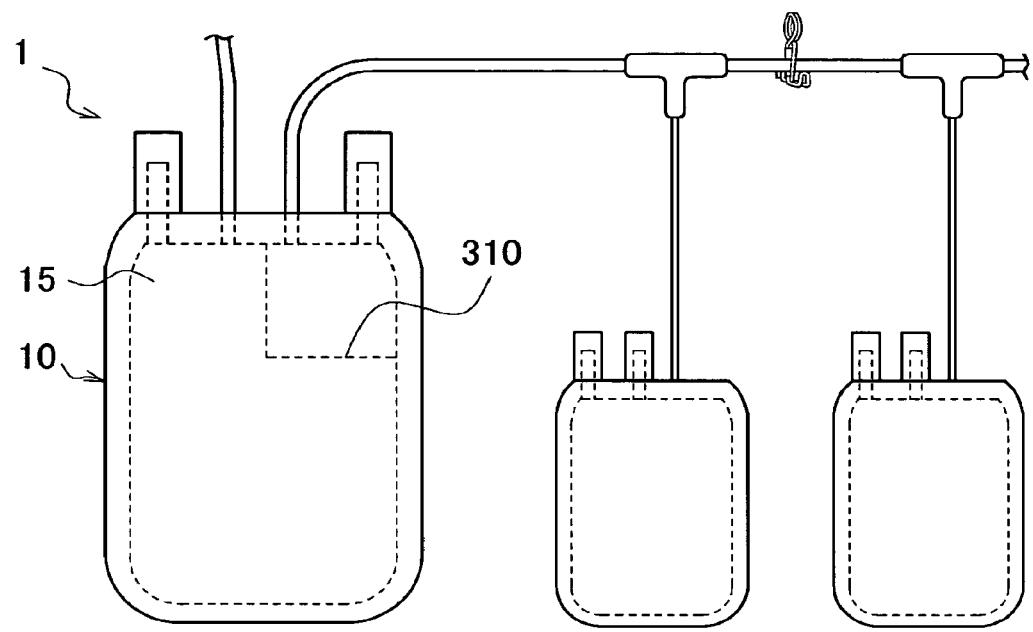
FIG. 31 is a schematic view illustrating a constitution of the serum preparation apparatus according to a sixteenth Embodiment.

FIG. 31 shows a constitution having a function that is substantially identical to the blood reservoir 10 shown in FIG. 1, but it is different in that a temporal partition 310 to be a divider is provided so as not to cause entry of the blood in the vicinity of the serum outlet during preparation of the serum. When the blood enters and coagulates in the vicinity of the serum outlet, recovery of the serum may be difficult. Alternatively, the coagulated blood may be contaminated in the serum to be preserved. The temporal partition 310 is provided to be removable after preparing the serum so that the serum can be transferred from the serum outlet to the preservation bag. Suggested temporal partition 310 may be a closure by a clamp, or a closure with easy peel or the like. The temporal partition 310 may be of any mode as long as it can isolate the outlet and the vicinity thereof from the blood during preparation of the serum, while the isolation can be released upon removal of the serum, if necessary.

Seventeenth Embodiment

Figure 32:
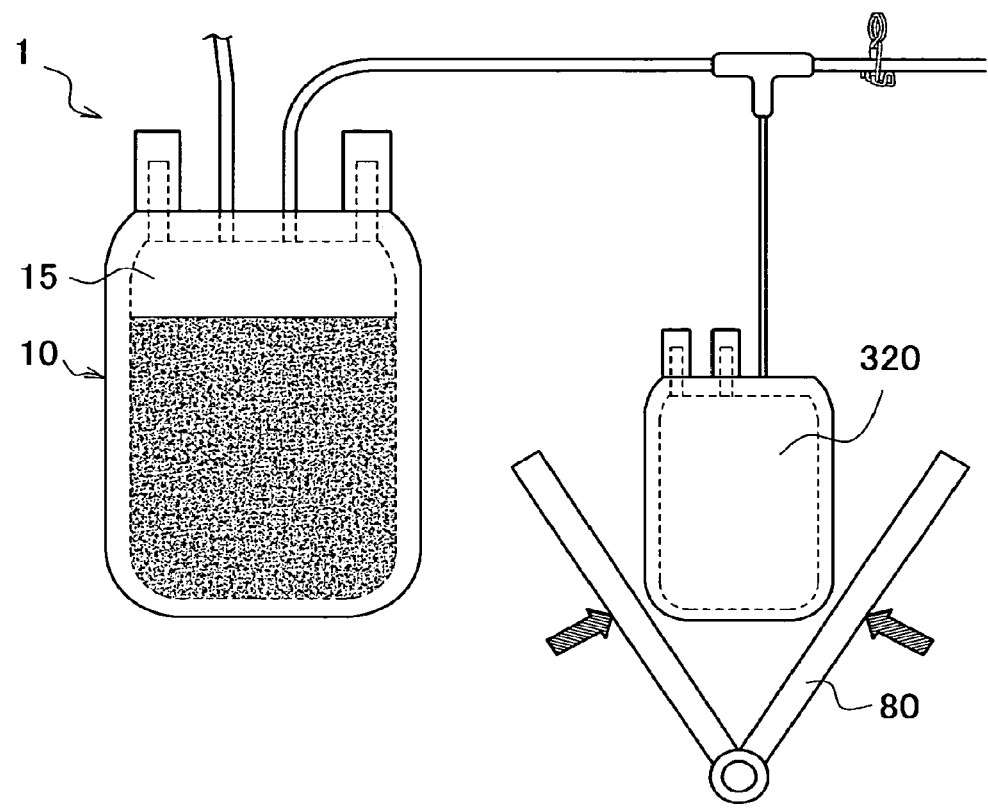
FIG. 32 is a schematic view illustrating a constitution of the serum preparation apparatus according to a seventeenth Embodiment.

FIG. 32 shows a constitution having a function that is substantially identical to the blood reservoir 10 shown in FIG. 1, but it is different in that a bag for flushing 320 is provided so as not to cause entry of the blood by the operation of preparing the serum in the vicinity of the serum outlet. When the blood enters and coagulates in the vicinity of the serum outlet, recovery of the serum may be difficult. Alternatively, the coagulated blood may be contaminated in the serum to be preserved.

A gas or a liquid is charged in the bag for flushing 320, and the blood adhered to the serum outlet and in the vicinity thereof (also including the coagulated blood) is flushed to eliminate therefrom.

The Embodiments 16 and 17 are particularly advantageous in the case in which the serum preparation bag of the Embodiment 18 without having the glass processed body described below is used because the absence of the glass processed body may result in floating of the coagulated components which may adhere in the vicinity of the serum outlet as the case may be, although the coagulated components adhere to the glass processed body when the glass processed body is provided thereby being capable of preventing the adherence of the coagulated components in the vicinity of the serum outlet.

Eighteenth Embodiment

In this Embodiment, the glass processed body is not provided in the blood reservoir 10 shown in FIG. 1, and the serum is prepared by leaving the collected blood to stand in the empty bag. Then, the prepared serum is transferred to the preservation bag, and is divided into a plurality of preservation bags and is preserved.

Nineteenth Embodiment

In this Embodiment, the extensively researched aspect for preventing the glass processed body shown in FIG. 1 from entering into the tube 42 and the like to evoke possible interference of transfer of the serum is specifically explained.

First, the relationship between diameters of the glass processed body and of the tube forming the transfer path is defined so that the diameter of the glass processed body becomes greater than the internal diameter of the tube. Accordingly, invasion of the glass processed body into the tube 42 and the like can be prevented. For example, the diameter of the beads is preferably greater than the internal diameter of the tube by approximately 1 mm to 5 mm. Thus, when the internal diameter of the tube is 3 mm, the beads preferably have a diameter of approximately 4 mm.

Figure 33:
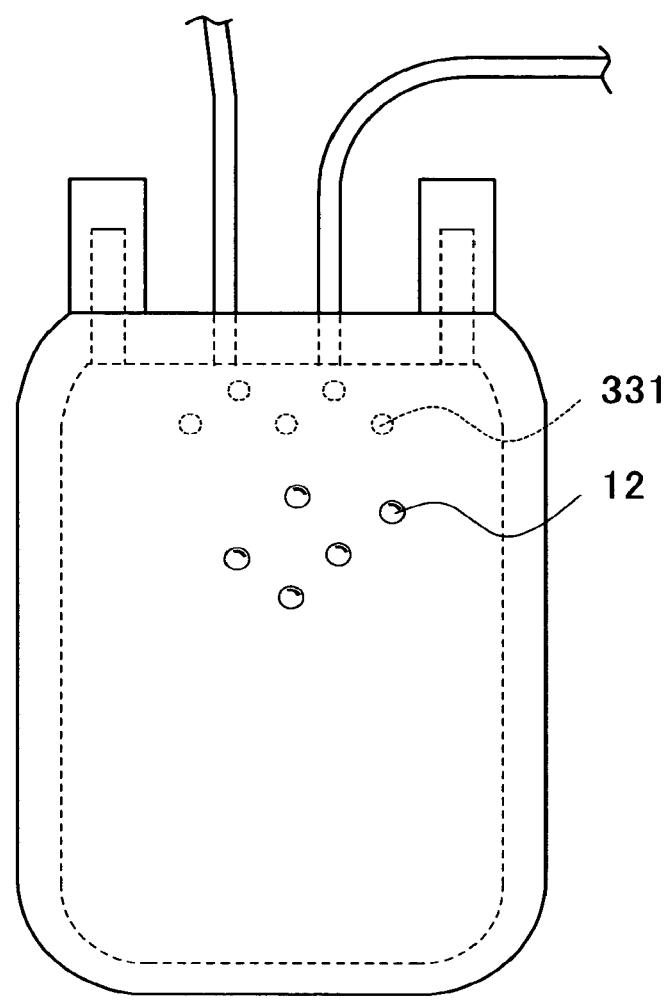
FIG. 33 is a schematic view illustrating a constitution of the serum preparation apparatus according to a nineteenth Embodiment.
Figure 34:
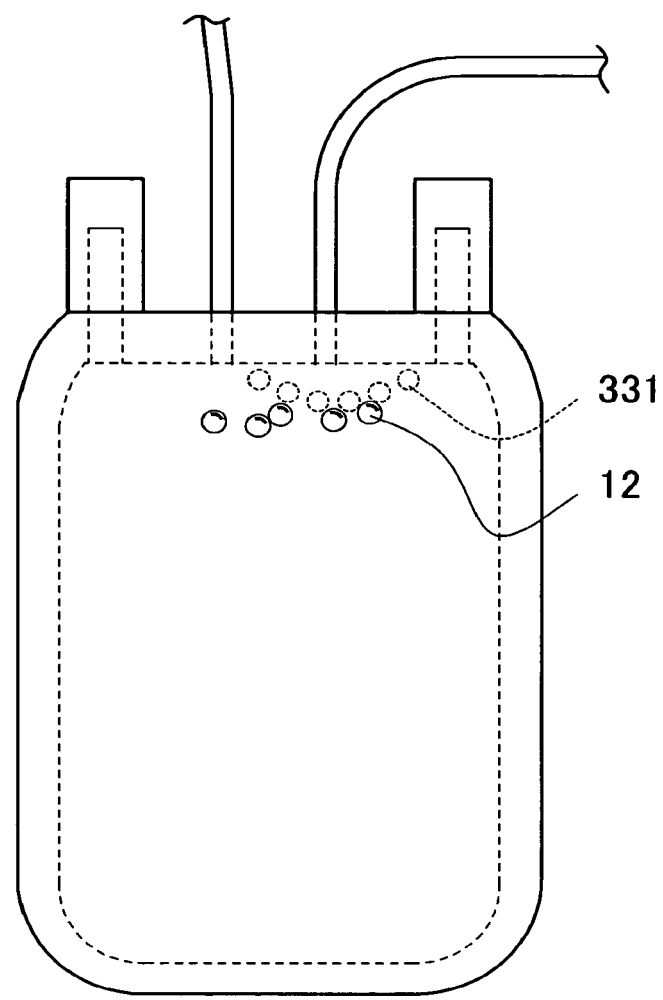
FIG. 34 is a schematic view illustrating a constitution of the serum preparation apparatus according to the nineteenth Embodiment.
Figure 35:
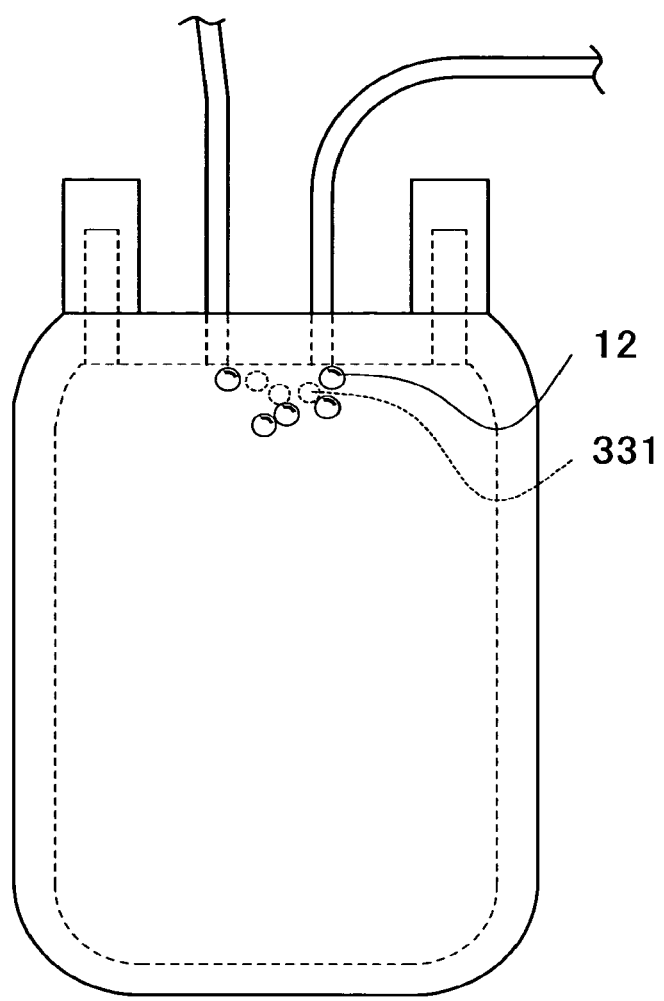
FIG. 35 is a schematic view illustrating a constitution of the serum preparation apparatus according to the nineteenth Embodiment.

Next, as shown in FIG. 33, a plurality of spot welding parts 331 may be formed in the vicinity of the serum output tube port (formed by thermal welding). Accordingly, transfer of the glass can be prevented. Interval between spot welding parts 331 herein is smaller than the diameter of the beads. Furthermore, the number of the spots is desirably equal to or greater than number of the beads, because the beads completely occlude the flow channel for removing the serum when the number of the beads is smaller than the number of the spots as shown in FIG. 35, thereby leading to unsecured flow channel for removing the serum. In contrast, when the number of spots is equal to or greater than the number of the beads as shown in FIG. 34, the beads do not completely occlude the flow channel for removing the serum, thereby leading to ensured flow channel for removing the serum without fail.

Each Embodiment described in the foregoing can be perfected alone, as a matter of course, but each may be also performed in combination freely. Practice of the present invention is not limited to single Embodiment. Additionally, the prepared serum may be used to culture cells collected from a patient, which cells may be transplanted into the patient, and transfusion of the prepared hemocyte components to the patient may be also carried out. Accordingly, they can also be used in regenerative medicine.

Hereinafter, the present invention will be explained in more detail, but the present invention is not in any way limited to these Examples.

Results of study on efficacy of the serum prepared using the blood component separator according to the first Embodiment, efficacy of recovered erythrocyte, and proliferation of stem cells will be explained below. In the experiments, an exterior package made of polyvinylchloride was used.

Example 1

Determination of Activation Promoting Effect

Large and small glass processed bodies consisting of soda glass were added to a blood storage part under the conditions shown in Table 1, respectively. To this blood storage part was charged 20 ml of fresh human blood. It was incubated while stirring, and each 1.5 ml was collected in 10, 20, 30, 60 and 90 minutes thereafter. Then, the number of the platelets was counted. For the stirring, a stirring (shaking) apparatus (Multi Shaker MMS-300, manufactured by Tokyo Rikakikai Co., Ltd.) was used, and for the counting of hemocytes, a hematology analyzer (Multiparameter automated hematology analyzer K-4500, manufactured by SYSMEX CORPORATION) was used.

TABLE 1

| | Sample | | | | | | | | |
|---|---|---|---|---|---|---|---|---|---|
| | A | B | C | D | E | F | G | H | I |
| | | | | | Diameter | | | | |
| | — | 1 mm (4 mm²/number) | | | | φ 4 mm (50 mm²/number) | | | |
| Number | 0 | 1 | 3 | 5 | 10 | 1 | 3 | 5 | 10 |
| Ratio of glass surface area per 1 mL of blood (mm²/mL) | 0 | 0.2 | 0.6 | 1.0 | 2.0 | 2.5 | 7.5 | 12.5 | 25.0 |

Figure 16:
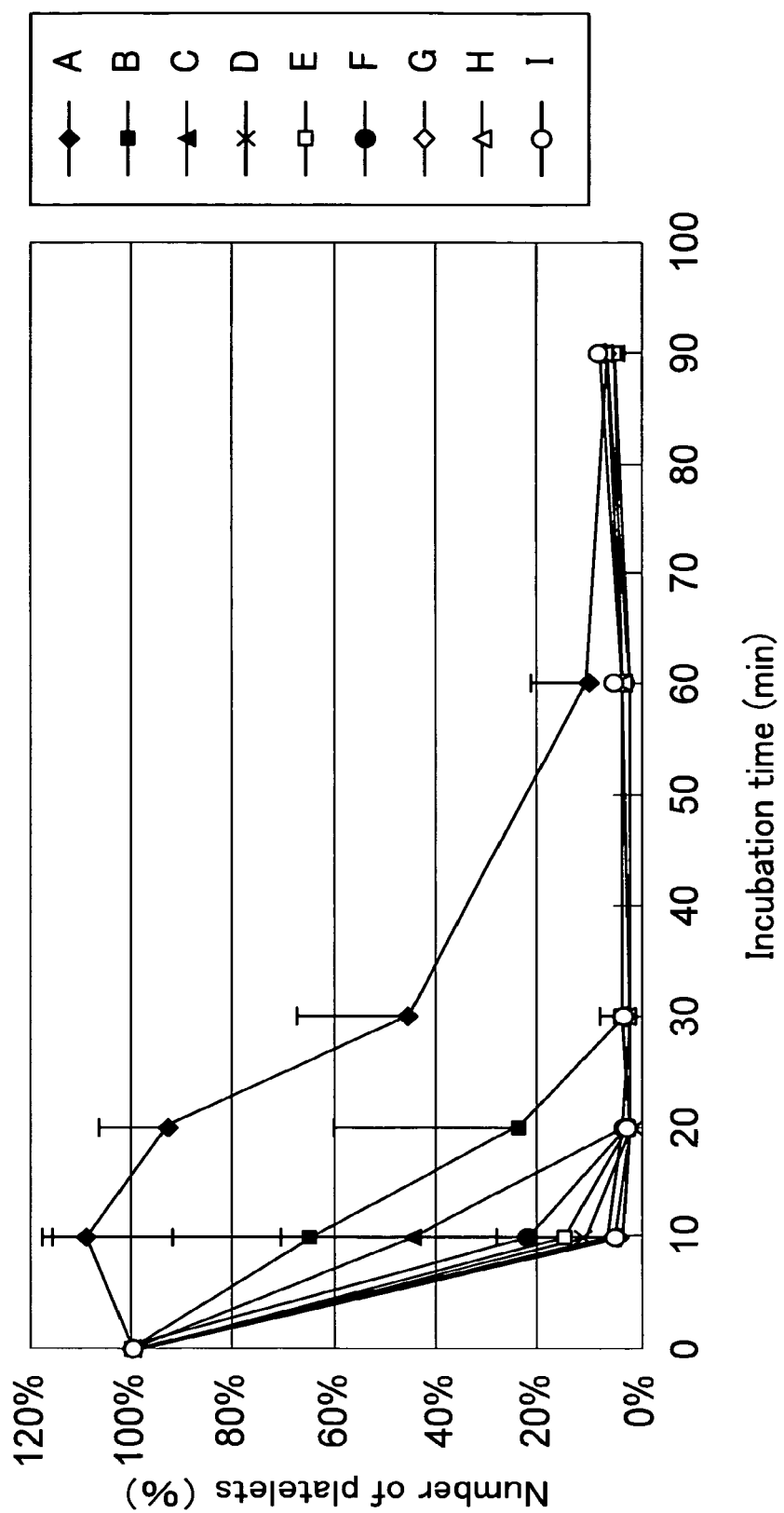
FIG. 16 is a characteristic view illustrating a relationship between time elapsed following collection of the blood and residual ratio of the platelets according to Example 1.

FIG. 16 shows a relationship between number of platelets and incubation time. This reveals that the platelets are more significantly activated with the greater ratio of surface area of the glass processed body per 1 ml of the blood to result in agglutination. Also, it was revealed that a sample to which no glass processed body was added takes considerable time, i.e., about 90 min, until blood agglutination was observed. Furthermore, provided that the glass processed body was not added followed by leaving to stand for a long period of time to facilitate release of the growth factor from the platelets, the serum is often coagulated or a large amount of fibrin may be deposited in the following process, due to insufficient activation of other coagulation factors. Thus, in the container of samples B to I according to Experimental Example, the platelets can be rapidly agglutinated because the glass processed body was stored, suggesting that growth factors derived from the platelets which will be required for preparation of the serum can be released at high efficiency.

Example 2

Determination of Growth Factor Releasing Effect

Figure 17:
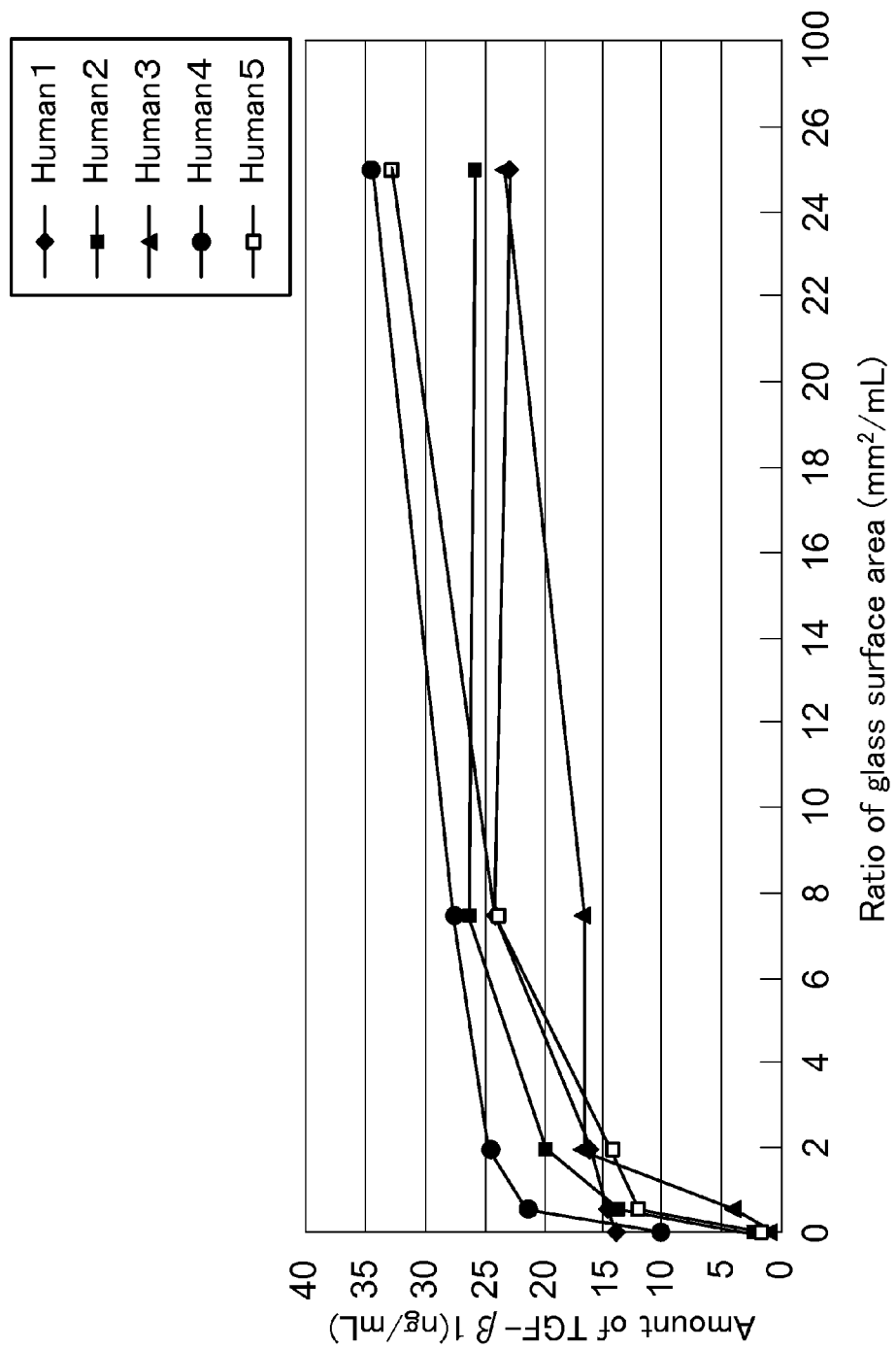
FIG. 17 is a characteristic view illustrating a relationship between the area of the glass processed body in contact with the blood and amount of release of a cell growth factor (TGF-β1) into the serum according to Example 2.
Figure 18:
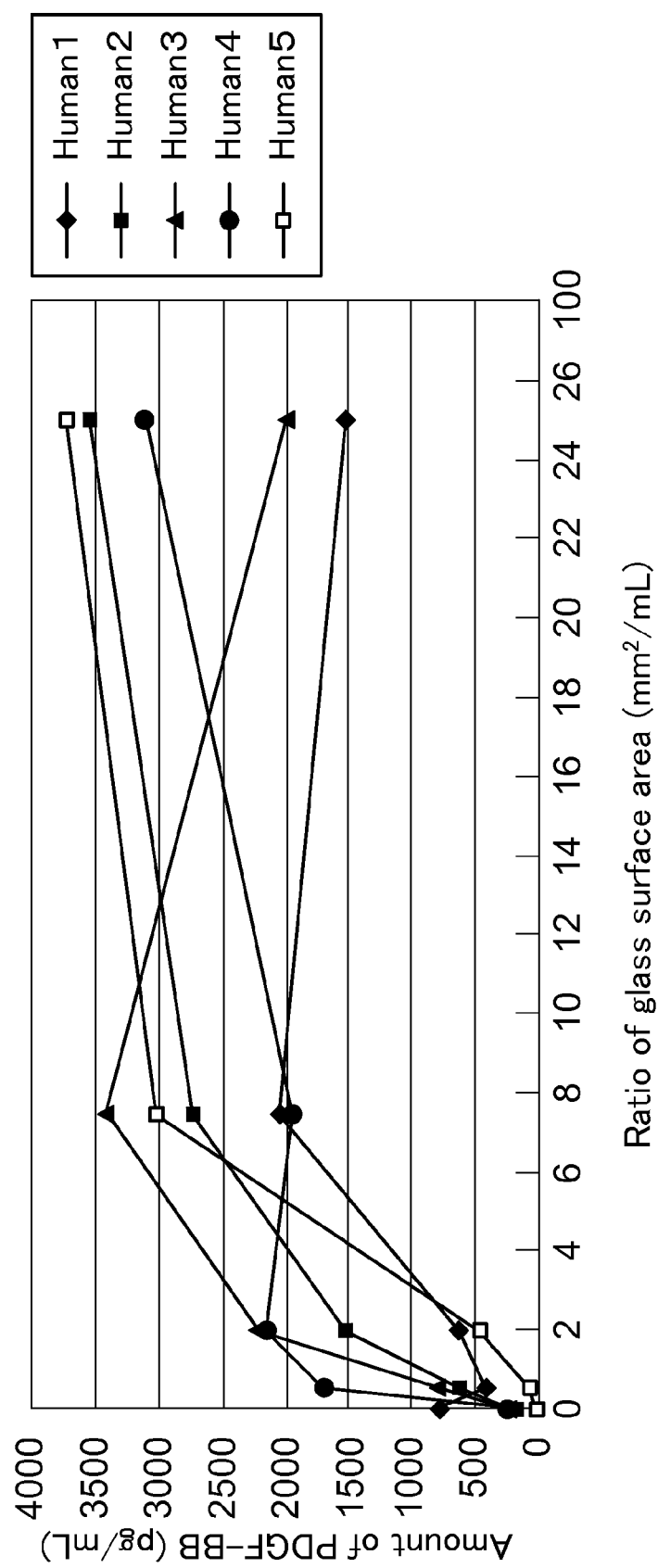
FIG. 18 is a characteristic view illustrating a relationship between the area of the glass processed body in contact with the blood and amount of release of a cell growth factor (PDGF-BB) into the serum according to Example 2.

Study of effect on release of growth factor was conducted. Five samples among 9 samples used in Example 1 were selected, and fresh blood from 5 subjects was added to each sample. Measurement of the growth factor after 20 minutes elapsed is performed. Specifically, after incubation under conditions shown in Table 2 below by the method that is similar to Example 1, amount of the growth factors (TGF-β1, PDGF-BB) was measured by a commercially available test kit (manufactured by R&D SYSTEMS, Inc.) using a microplate reader (manufactured by Multiskan BICHROMATIC Labsystem). The measurement was represented as a ratio to the amount in the specimen having a contact area of 0 with the glass processed body. The results are illustrated in FIG. 17 and FIG. 18. In the Figures, the abscissa shows the surface area of the glass, and the ordinate shows the amount of each growth factor. As is clear from the FIG. 17, amount of release of the growth factor was significantly increased when only a slight amount of the glass processed body, i.e., 0.6 mm² per 1 ml of the blood was added. However, it was demonstrated that the amount of TGF-β1 achieves approximate equilibrium when the ratio of the surface area was enormously increased. Furthermore, in FIG. 18, significant increase in the growth factor was found by merely adding the glass processed body in just a slight amount. Moreover, it was found that the amount of PDGF-BB achieves approximately equilibrium when the ratio of the surface area was enormously increased, similarly to FIG. 17.

TABLE 2

| | Sample | | | | |
|---|---|---|---|---|---|
| | A | C | E | G | I |
| | | | Diameter | | |
| | — | 1 mm | | 4 mm | |
| Number | 0 | 3 | 10 | 3 | 10 |
| Ratio of glass surface area per 1 mL of blood (mm²/mL) | 0 | 0.6 | 2.0 | 7.5 | 25.0 |

Example 3

Test of Hemolyzing Properties by Glass Processed Body

Examples 1 and 2 demonstrated that addition of the glass processed body is effective in activation of platelets and increase of growth factors. However, there was concern that addition of the glass processed body may cause hemolysis during preparation of the serum. Thus, the relationship between the amount of addition of the glass processed body and hemolysis was studied.

Figure 19:
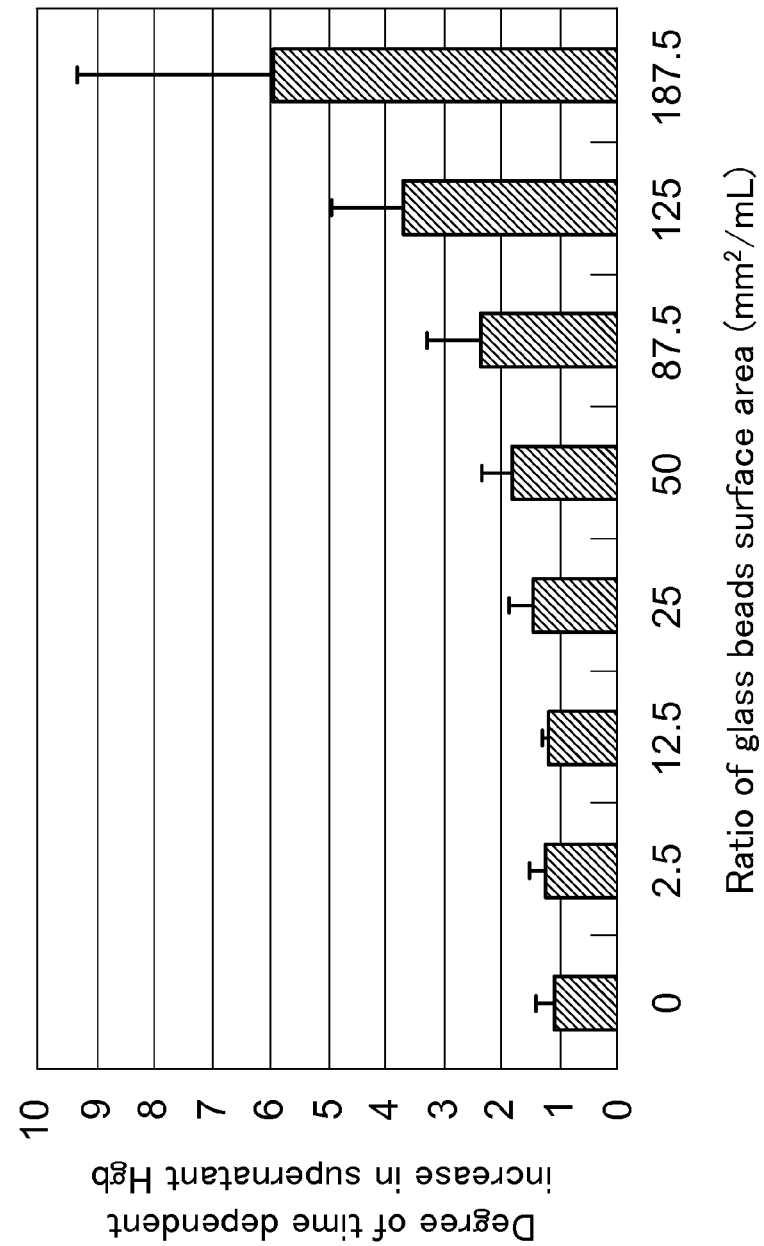
FIG. 19 is a characteristic view illustrating a relationship between the area of the glass processed body in contact with the blood and amount of release of hemoglobin into the supernatant according to Example 3.

Prepared bovine blood was added to each of the samples A, F, H, and I used in Example 1 and samples J to M prepared to have a wide range of the ratio of glass surface area per 1 ml of the blood, and incubated while stirring. Sampling thereof was conducted in a time dependent manner, and concentration of hemoglobin in the supernatant obtained by centrifugal separation was measured (Hemoglobin B-test Wako, manufactured by Wako Pure Chemical Industries, Ltd.). Results following the incubation for 90 minutes are illustrated in FIG. 19. It was demonstrated that increase rate of hemoglobin in the supernatant is elevated as the surface area of the glass processed body stored inside of the blood reservoir is increased. This indicates that the glass processed body had an excessive contact area with the blood, and accounted for disruption of erythrocytes (hemolysis) in the activation promoting step or the centrifugal separation step very often. However, it was also demonstrated that the hemolyzing property that is equal to the sample A without addition of the glass processed body was exhibited up to 12.5 mm$^2$.

TABLE 3

| Sample | A | F | H | I | J | K | L | M |
|---|---|---|---|---|---|---|---|---|
| Number (4 mm diameter) | 0 | 1 | 5 | 10 | 20 | 35 | 50 | 75 |
| Ratio of glass surface area per 1 mL of blood (mm$^2$/mL) | 0 | 2.5 | 12.5 | 25 | 50 | 87.5 | 125 | 187.5 |

Example 4

Determination of Proliferation of Rat Stem Cell

Blood collected from a human was shaken for 20 minutes in a blood reservoir in which any one of the aforementioned glass processed bodies was stored, with the contact area of the glass processed body per 1 ml of the blood being adjusted to 0 mm$^2$ or 1.5 mm$^2$. The blood after completing shaking was centrifuged (conditions of centrifugal separation: 2250 g×10 min, 4° C.) to isolate the supernatant. After subjecting the supernatant to a heat treatment at 56° C. for 30 minutes, the liquid was filtrated with a 0.22 μm filter, and preserved at −80° C. The supernatant was thawed upon cell culture, and added to a medium for cell culture. The cells subjected to this Example were cells derived from bone marrow which were prepared by previously culturing cells obtained from rat femur bone marrow to give adhesive cells. Tens of thousands of cells per well were inoculated and cultured using a medium to which the supernatant obtained by adding the glass processed, the supernatant obtained without adding the glass processed body, or a commercially available fetal bovine serum for cell culture was added to give a concentration of 10%. On days 1, 3, and 7 after initiating the culture, the cell number was counted. Results obtained by determining the effects on cell proliferation are illustrated in FIG. 20.

Figure 20:
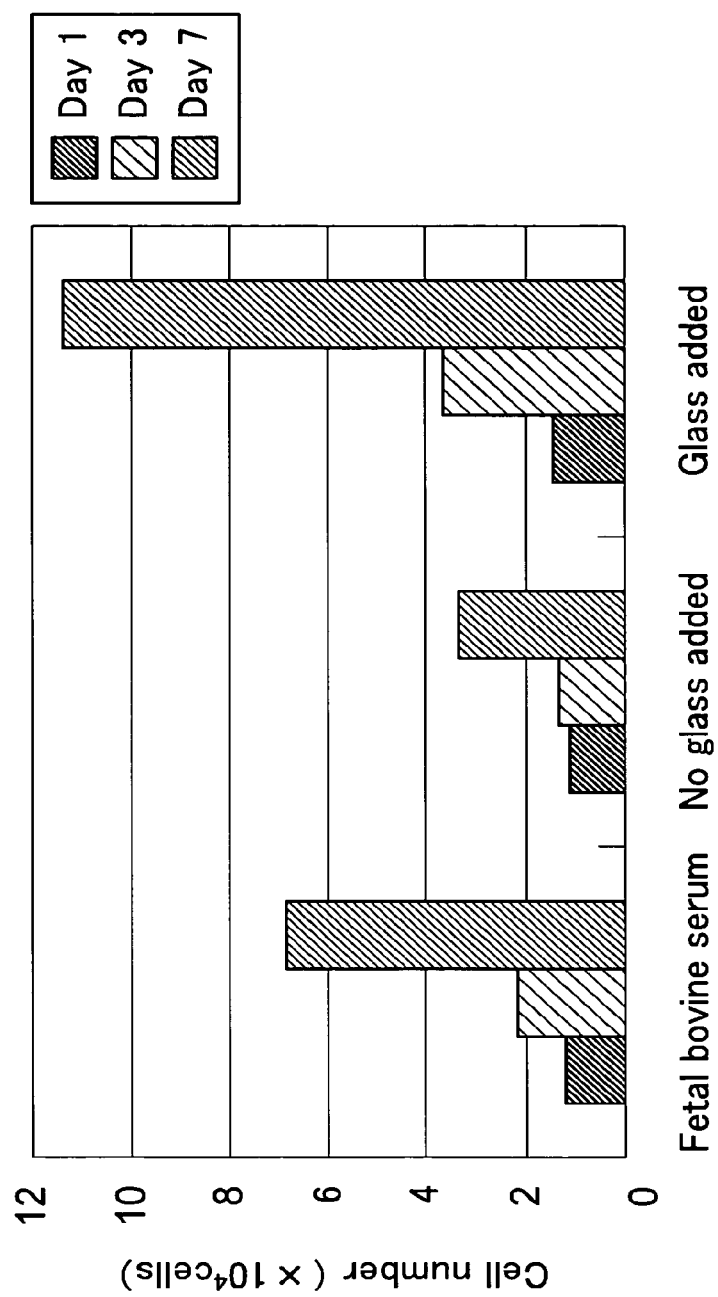
FIG. 20 is a view illustrating a relationship between each sample and cell number according to Example 4.

As shown in FIG. 20, it is revealed that presence or absence of contact with the glass processed body during preparation of the serum which is added upon culture of the cells derived from rat bone marrow markedly affect the cell proliferation performance. Also, a more favorable result was obtained with the supernatant obtained by adding the glass processed body, in comparison with the fetal bovine serum which had been generally used hitherto.

Example 5

Recovery of Erythrocytes

Figure 21:
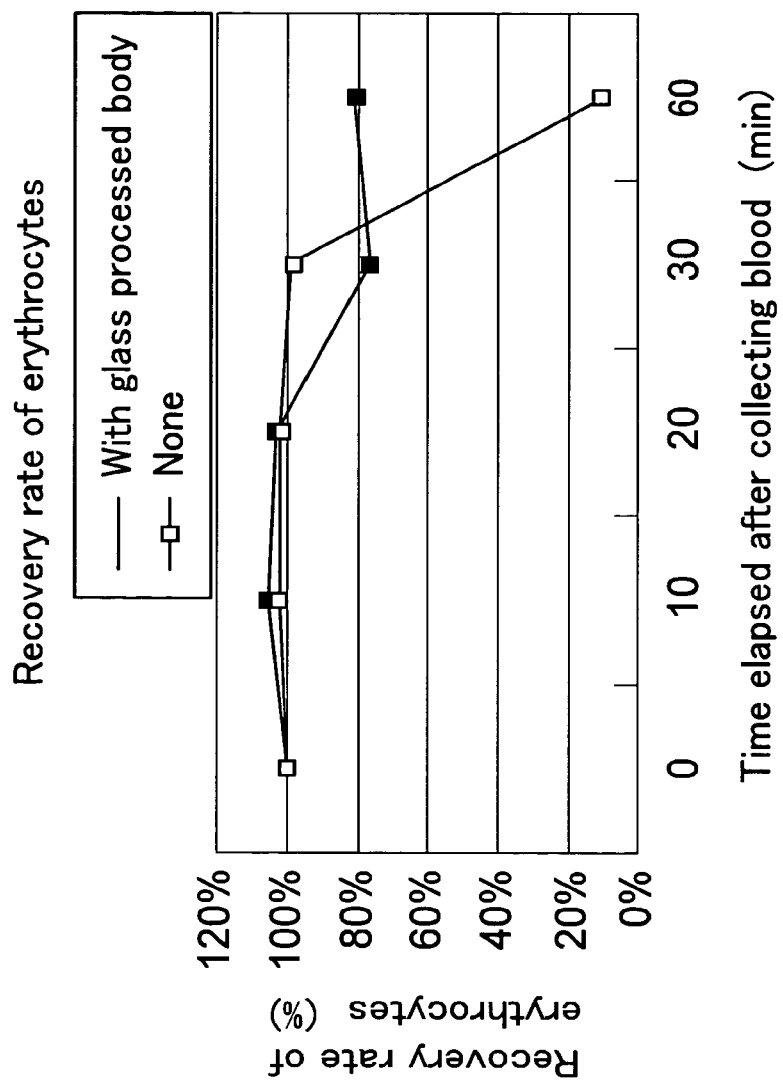
FIG. 21 is a view illustrating time dependent alteration of recovery rate of erythrocytes of each sample according to Example 5.

Ascertainment of recovered erythrocytes was carried out. Contact area of the glass processed body was adjusted to be 12.5 mm$^2$ per 1 ml of the blood, and 20 ml of blood was collected, followed by shaking while stirring with Multi Shaker MMS-300 (manufactured by Tokyo Rikakikai Co., Ltd.) for 60 min. The blood collected in a test tube and left to stand for the same time period according to a conventional method of preparation of a serum was used as a control, and time dependent alteration of number of the erythrocytes was determined. The results are illustrated in FIG. 21. When number of the erythrocytes immediately after collecting the blood was assumed to be 100%, about 80% of the erythrocytes remained after shaking with the glass processed body for 60 min. On the other hand, when the serum was collected with a conventional method, a large fraction of the blood in the container formed a clot, and thus only 10% of the erythrocytes were recovered in 60 minutes after collecting the blood.

Example 6

Recovery of Serum from Platelet-Rich Plasma (PRP)

Possibility of preparing a serum containing a large amount of growth factors was verified also from the blood which had been collected previously using an anticoagulant such as a CPD solution, or from platelet-rich plasma (PRP) prepared by apheresis. Fresh human blood to which CPD was added to yield a final concentration of 12.2% was prepared. This CPD-added blood was centrifuged under a condition of 760 g, for 10 min (22° C.) to prepare platelet-rich plasma. Incubation of 0.8 mL of thus resulting platelet-rich plasma in a vessal to which calcium chloride and glass processed body were previously added as shown in Table 4 was initiated at 37° C., and the container was shaken freely. The time period was measured which elapsed following the addition of the platelet-rich plasma until the time point when fibrin was deposited from the platelet-rich plasma, resulting in lowering of fluidity in appearance. Each specimen with lowered fluidity was immediately centrifuged under a condition of 2,250 g, for 10 minutes (4° C.), and the resulting supernatant was isolated. Thereafter, the amount of PDGF-BB and the amount of TGF-β1 included in this supernatant were measured. Thus the measured amount of each growth factor is illustrated in FIG. 22 as a ratio (%) to the amount of each growth factor included in the serum prepared from the identical blood.

TABLE 4

| | Specimen | | |
|---|---|---|---|
| | 1 | 2 | 3 |
| Amount of added calcium chloride | | 0.01 mM | |
| Amount of added glass processed body | 0 mm$^2$ | 40 mm$^2$ | 80 mm$^2$ |

Figure 22:
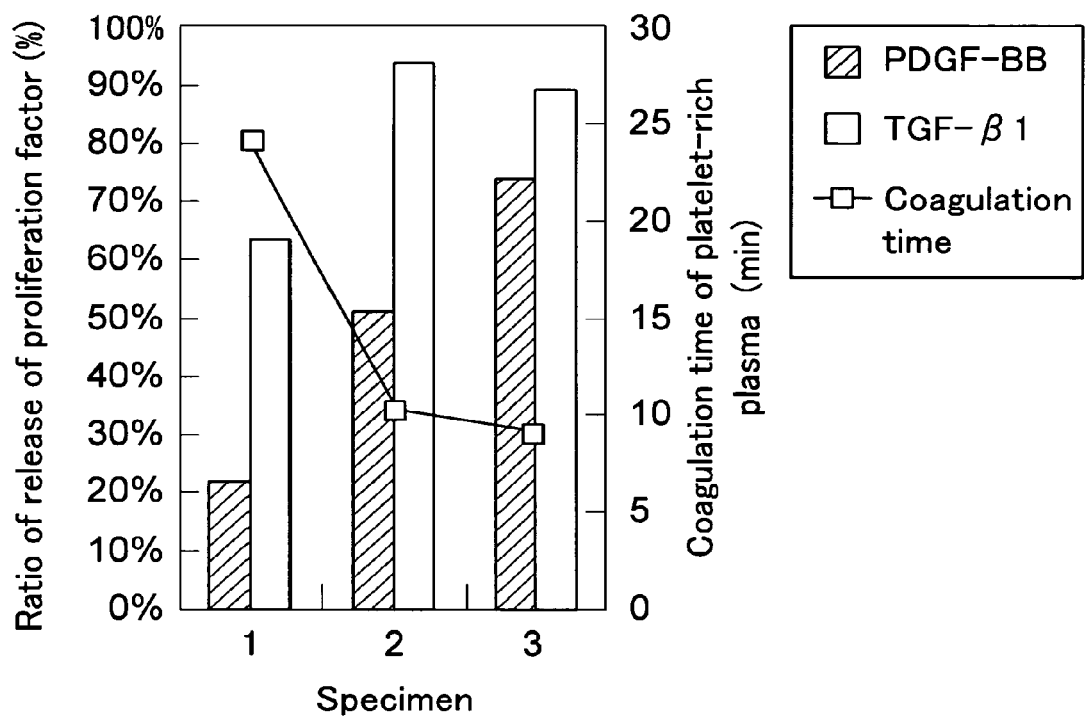
FIG. 22 is a view illustrating ratio of release of a growth factor and coagulation time of platelet-rich plasma of each specimen according to Example 6.

By adding the glass processed body in the amount of addition as shown in FIG. 22, or by increasing the area, coagulation time of the platelet-rich plasma was shortened, and the amount of release of PDGF-BB and TGF-β1 was also increased.

Example 7

Determination of Effect of Addition of Air

Air or the glass processed body was added to the blood storage part under the conditions shown in Table 5, respectively. To this blood storage part was charged 20 ml of fresh human blood, and incubated while stirring with Multi Shaker MMS-300 (manufactured by Tokyo Rikakikai Co., Ltd.). Number of platelets after 20 minutes elapsed was counted using Multiparameter automated hematology analyzer K-4500 (manufactured by SYSMEX CORPORATION).

TABLE 5

| Specimen | 1 | 2 | 3 | 4 | 5 | 6 | 7 |
|---|---|---|---|---|---|---|---|
| Total area of added glass processed body (mm$^2$) | 0 | 0 | 0 | 0 | 50 | 50 | 50 |
| Total quantity of added air (cc) | 0 | 2.5 | 5.0 | 20 | 2.5 | 5.0 | 20 |

Figure 23:
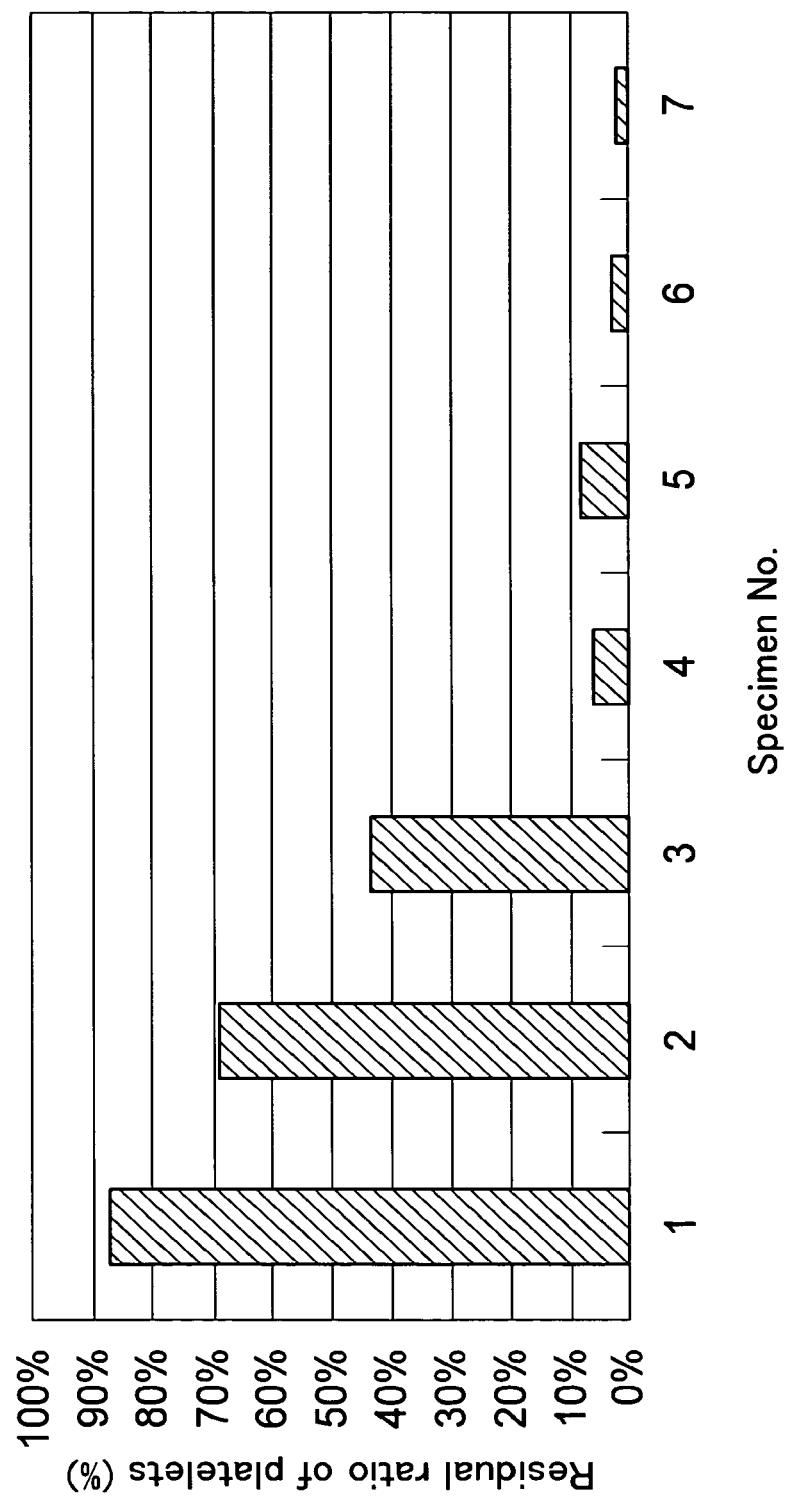
FIG. 23 is a view illustrating residual ratio of platelets in each specimen according to Example 7.

As shown in FIG. 23, in the specimen 1 prepared without adding either the glass processed body or the air, approximately 90% of the platelets remained even after a lapse of 20 minutes. When the air alone was added (specimens 2 to 4), residual ratio of the platelets decreased in proportion as the quantity of the added air. Additionally, when the glass processed body and the air were used in combination, decrease in residual ratio of the platelets was remarkable, and proportional correlation was found between the quantity of the added air and the residual ratio of the platelets. Therefore, it was suggested that the air alone also exerted the effect of promoting the activation and agglutination of platelets although not comparative to the glass processed body, and that the air in combination with the glass processed body achieves the effect to further promote the activation and coagulation of the platelets.

The aforementioned Example 1 revealed that to store the glass processed body as a blood coagulation accelerating substance in the blood reservoir is effective for allowing the platelets to coagulate rapidly. More specifically, when the blood reservoir including the glass processed body stored therein is used, growth factors derived from the platelets which will be necessary for preparing a serum from the collected blood can be produced quickly with high efficiency. Therefore, when such a glass processed body is stored in the blood component separator, a large amount of serum can be quickly prepared (produced).

Moreover, Example 2 verified that growth factors that are useful in cell proliferation are sufficiently released during the preparation step into the serum prepared from the blood collected in a container in which the glass processed body was stored therein, and consequently, addition of the serum to a medium contributes to proliferation of cells derived from bone marrow. Therefore, storage of the glass processed body in the blood component separator is advantageous in preparation of a serum that is effective in promotion of cell proliferation.

Furthermore, Example 3 revealed that storage of excess glass processed body in the blood reservoir is not desirable in light of amount of hemoglobin released in the supernatant of the serum separated in the centrifugal separation step, because such storage may lead to disruption of erythrocytes (hemolysis) during shaking and centrifugal separation.

Additionally, Examples 4 to 7 showed that after preparing the serum that effectively acts on cell cultures, a large fraction of erythrocytes could be recovered as individually isolated cells, not in the state of a clot. This suggests that autologous blood can be preserved as blood for transfusion upon transplantation of stem cells to a patient with low volume of circulating blood or to a patient which receives transplant surgery which may be accompanied by heavy bleeding. Hence, preparation of the serum under shaking using a container for collecting blood in which the glass processed body is stored also enables recovery of components other than serum.

As in the foregoing, in connection with the glass processed body in the blood reservoir taking into account Examples 1 to 7, it is proven that the surface area of the glass processed body to the volume of reservable blood in the container is desirably defined to have a relationship of 0.1 mm$^2$/ml or greater in light of promotion of the activation of platelets and coagulation factors and recovery of growth factors, and is preferably defined to have a relationship of 25.0 mm$^2$/ml or less also in light of factors of occurrence of hemolysis.

INDUSTRIAL APPLICABILITY

As explained hereinabove, the blood component separator of the present invention can prepare a serum quickly and in a large amount in which propagation of microorganisms is suppressed. Thus, it is suited for preparation of a large amount of serum which may be used for stem cell culture in regenerative medicine.

The invention claimed is:

1. A blood component separation storage apparatus for separating a plurality of blood components of blood so as to be stored therein, the blood component separation storage apparatus comprising:
a blood reservoir for holding the blood; and
a component storage part connected to the blood reservoir aseptically and in an air-tight manner, wherein:
the blood reservoir contains an anticoagulant which suppresses coagulation of the blood; the component storage part is provided with a plurality of bags connected together aseptically and in an air-tight manner;
a part of the plurality of blood components contained in the blood in the blood reservoir is separated and stored in a first bag of the plurality of bags, the first bag containing a blood coagulation accelerating substance which is brought into contact with the part of the blood components stored in the first bag and a neutralizing agent which neutralizes the anticoagulant; and
the blood coagulation accelerating substance is insoluble in the blood and has a spherically shaped body made with a silicon dioxide compound, and has a surface area of 0.1 mm$^2$ to 25 mm$^2$ per 1 ml of blood.

2. The blood component separation storage apparatus according to claim 1, wherein fractionation of a serum and other components is conducted in the component storage part.

3. The blood component separation storage apparatus according to claim 1, wherein the blood coagulation accelerating substance is a granulated substance capable of activating platelets in the blood and of letting fiber in the blood adhere to surfaces of the platelets.

4. The blood component separation storage apparatus according to claim 1, wherein the blood coagulation accelerating substance is a solid having a specific gravity greater than the blood, the blood coagulation accelerating substance settling out downwardly so that a serum and coagulation factors are fractionated.

5. The blood component separation storage apparatus according to claim 1, wherein at least one kind selected from the group consisting of a CPD solution and an ACD-A solution is contained as the anticoagulant.

6. The blood component separation storage apparatus according to claim 1, wherein the neutralizing agent contains at least calcium ions.

* * * * *